United States Patent
Thaning

(10) Patent No.: US 8,920,780 B2
(45) Date of Patent: Dec. 30, 2014

(54) CONTRAST AGENTS

(75) Inventor: Mikkel Thaning, Oslo (NO)

(73) Assignee: GE Healthcare AS, Oslo (NO)

( * ) Notice: Subject to any disclaimer, the term of this patent is extended or adjusted under 35 U.S.C. 154(b) by 603 days.

(21) Appl. No.: 12/665,792

(22) PCT Filed: Jul. 4, 2008

(86) PCT No.: PCT/NO2008/000255
§ 371 (c)(1),
(2), (4) Date: Dec. 21, 2009

(87) PCT Pub. No.: WO2009/008734
PCT Pub. Date: Jan. 15, 2009

(65) Prior Publication Data
US 2010/0322868 A1 Dec. 23, 2010

(30) Foreign Application Priority Data

Jul. 12, 2007 (NO) .................................. 20073594
Jul. 12, 2007 (NO) .................................. 20073595

(51) Int. Cl.
*A61K 49/00* (2006.01)
*A61K 49/04* (2006.01)

(52) U.S. Cl.
CPC ................................ *A61K 49/0433* (2013.01)
USPC ........................................... 424/9.1; 424/9.4

(58) Field of Classification Search
USPC .................................... 424/9.4, 9.1
See application file for complete search history.

(56) References Cited

U.S. PATENT DOCUMENTS

| 3,763,226 A | 10/1973 | Ingelman |
| 5,349,085 A | 9/1994 | Hansen et al. |
| 5,993,780 A * | 11/1999 | Almen et al. .............. 424/9.452 |
| 2005/0281746 A1 | 12/2005 | Melton et al. |

FOREIGN PATENT DOCUMENTS

| EP | 0023992 | 2/1981 |
| EP | 0108638 | 5/1984 |
| WO | 88/09328 | 12/1988 |
| WO | 94/14478 | 7/1994 |
| WO | 94/22811 | 10/1994 |
| WO | 97/00240 | 1/1997 |
| WO | 2009/008734 | 1/2009 |

OTHER PUBLICATIONS

PCT/NO2008/000255 ISRWO dated Sep. 2009.

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention relates to a class of compounds and to diagnostic compositions containing such compounds where the compounds are iodine containing compounds. More specifically the iodine containing compounds are chemical compounds containing two linked iodinated phenyl groups of the general formula R—N(CHO)—X—N($R^3$)—R wherein X denoted an optionally substituted alkylene group, $R^3$ denotes a hydrogen atom or an acyl function and each R denotes a triiodinated phenyl residue further substituted by hydrophilic moieties. The invention also relates to the use of such diagnostic compositions as contrast agents in diagnostic imaging and in particular in X-ray imaging, and to contrast media containing such compounds.

19 Claims, No Drawings

CONTRAST AGENTS

This application is a filing under 35 U.S.C. 371 of international application number PCT/NO2008/000255, filed Jul. 4, 2008, which claims priority to Norwegian application numbers 20073595 filed Jul. 12, 2007 and 20073594 filed Jul. 12, 2007, the entire disclosure of each of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing two linked iodinated phenyl groups.

The invention also relates to the use of such diagnostic compositions as contrast agents in diagnostic imaging and in particular in X-ray imaging, and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade mark Gastrografen™), ionic dimers such as ioxaglate (marketed e.g. under the trade mark Hexabrix™), nonionic monomers such as iohexol (marketed e.g. under the trade mark Omnipaque™) iopamidol (marketed e.g. under the trade mark Isovue™), iomeprol (marketed e.g. under the trade mark Iomeron™) and the non-ionic dimer iodixanol (marketed under the trade mark Visipaque™).

The most widely used commercial non-ionic X-ray contrast agents such as those mentioned above are considered safe. Contrast media containing iodinated contrast agents are used in more than 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of production, storage and administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in mg iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds, is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

In patients with acute renal failure, nephropathy induced by contrast medium remains one of the most clinically important complications of the use of iodinated contrast medium. Aspelin, P et al, The New England Journal of Medicine, Vol. 348:491-499 (2003) concluded that nephropathy induced by contrast medium may be less likely to develop in high risk patients when iodixanol is used rather than a low-osmolar, non-ionic contrast medium.

The part of the patient population considered as high risk patients is increasing. To meet the need for continuous improvement of in vivo X-ray diagnostic agents for the entire patient population, there is a continuous drive in finding X-ray contrast agents that has improved properties, also with regards to contrast induced nephrotoxicity (CIN).

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Relevant patent publications comprises EP 1186305, EP 686046, EP108638, EP 0049745, EP 0023992, WO 2003080554, WO2000026179, WO 1997000240, WO 9208691, U.S. Pat. Nos. 3,804,892, 4,239,747, 3,763,226, 3,763,227 and 3,678,152. At this time, one contrast medium having an iodinated non-ionic dimer as the active pharmaceutical ingredient is one the market, the product Visipaque™ containing the compound iodixanol. The compound Hexabrix™, containing the ionic dimeric compound ioxaglic acid is also on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose and any additional adverse effect known or discovered for such iodinated compounds. The agents should be stable under storage in dry form and/or in solution, and ease and economy in manufacture is an additional desired property.

SUMMARY OF THE INVENTION

The present invention provides compounds useful as contrast media having improved properties over the known media with regards to at least one of the criteria mentioned above and in particular to renal toxicity, osmolality, viscosity and solubility. The contrast media comprises iodine containing contrast enhancing compounds where iodine containing compounds are chemical compounds containing two linked iodinated phenyl groups. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

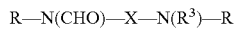

Formula (I)
and salts or optical active isomers thereof, wherein

X denotes a $C_3$ to $C_8$ straight of branched alkylene moiety optionally with one or two $CH_2$ moieties replaced by oxygen atoms, sulphur atoms or $NR^1$ groups and wherein the alkylene moiety optionally is substituted by up to six —$OR^1$ groups;

$R^1$ denotes a hydrogen atom or a $C_1$ to $C_4$ straight of branched alkyl group;

$R^3$ denotes a hydrogen atom or an acyl function; and each R independently is the same or different and denotes a triiodinated phenyl group, preferably a 2,4,6-triiodinated phenyl group, further substituted by two groups $R^2$ wherein each $R^2$ is the same or different and denotes a hydrogen atom or a non-ionic hydrophilic moiety, provided that at least one $R^2$ group in the compound of formula (I) is a hydrophilic moiety.

In formula (I) above, X preferably denotes a straight $C_3$ to $C_8$ alkylene chain optionally substituted by one to six —$OR^1$ groups. More preferred X denotes a straight $C_3$ to $C_5$ alkylene chain having at least one —$OR^1$ group, preferably at least one hydroxyl group in a position that is not vicinal to the bridge nitrogen atom. More preferably the alkylene chain is substituted by one to three hydroxyl groups and still more preferably the alkylene chain is a straight propylene, butylene or pentylene chain substituted by one, two or three hydroxyl groups. Particular preferred groups X comprises 2-hydroxy propylene, 2,3-dihydroxy butylene, 2,4-dihydroxy pentylene and 2,3,4-trihydroxy pentylene, and most particularly the 2-hydroxy propylene entity.

$R^1$ preferably denotes a hydrogen atom or a methyl group, most preferred a hydrogen atom.

The substituent $R^3$ preferably denotes a hydrogen atom or a residue of an aliphatic organic acid, and in particular a $C_1$ to $C_5$ organic acid such as formyl, acetyl, propionyl, butyryl, isobutyryl and valeriyl moieties. Hydroxylated and methoxylated acyl moieties are also feasible. In a particularly preferred embodiment the $R^3$ group in the compound of formula (I) denote a hydrogen atom, the formyl moiety or the acetyl moiety, most preferred the formyl moiety.

Each of the iodinated R groups can be the same or different and preferably denote a 2,4,6-triiodinated phenyl group, further substituted by two groups $R^2$ in the remaining 3 and 5 positions in the phenyl moiety.

The non-ionic hydrophilic moieties may be any of the non-ionizing groups conventionally used to enhance water solubility. Hence, the $R^2$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or $CH$ moieties replaced by oxygen or nitrogen atoms. The $R^2$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^2$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage, preferably amide linkages.

The $R^2$ groups of the formulas listed below are particularly preferred:

—CONH—CH$_2$—CH$_2$—OCH$_3$
—CONH—CH$_2$—CHOH—CH$_2$—OH
—CONN—CH$_2$—CHOCH$_3$—CH$_2$—OH
—CONH—CH$_2$—CHOH—CH$_2$—OCH$_3$
—CON(CH$_3$)CH$_2$—CHOH—CH$_2$OH
—CONH—CH—(CH$_2$—OH)$_2$
—CON—(CH$_2$—CH$_2$—OH)$_2$
—CON——(CH$_2$—CHOH—CH$_2$—OH)$_2$
—CONH—OCH$_3$
—CON (CH$_2$—CHOH—CH$_2$—OH) (CH$_2$—CH$_2$—OH)
—CONH—C(CH$_2$—OH)$_2$ CH$_3$,
—CONH—C(CH$_2$—OH)$_3$, and
—CONH—CH (CH$_2$—OH) (CHOH —CH$_2$—OH)
—NH(COCH$_3$)
—N(COCH$_3$) C$_{1-3}$ alkyl
—N(COCH$_3$)—mono, bis or tris-hydroxy C$_{1-4}$ alkyl
—N(COCH$_2$OH)—hydrogen, mono, bis or tris-hydroxy C$_{1-4}$ alkyl
—N(CO—CHOH—CH$_2$OH)—hydrogen, mono, bis or trihydroxylated C$_{1-4}$ alkyl.
—N(CO—CHOH—CHOH—CH$_2$OH)—hydrogen, mono, bis or trihydroxylated C$_{1-4}$ alkyl
—N(CO—CH—(CH$_2$OH)$_2$)—hydrogen, mono, bis or trihydroxylated C$_{1-4}$ alkyl; and
—N(COCH$_2$OH)$_2$ Even more preferably the R$^2$ groups will be equal or different and denote one or more moieties of the formulas —CONH—CH$_2$—CH$_2$—OH, —CONN—CH$_2$—CHOH—CH$_2$—OH, —CON(CH$_3$)CH$_2$—CHOH—CH$_2$OH, —CONH—CH—(CH$_2$—OH)$_2$ and —CON—(CH$_2$—CH$_2$—OH)$_2$. Still more preferably both R groups are the same and the R$^2$ groups in each R are the same or different and denote —CONH—CH$_2$—CH$_2$—OH, —CONH—CH$_2$—CHOH—CH$_2$—OH, CON(CH$_3$)CH$_2$—CHOH—CH$_2$OH, —CON—(CH$_2$—CH$_2$—OH)$_2$ and —CONH—CH—(CH$_2$—OH)$_2$. In a particularly preferred embodiment, both R groups are the same and all R$^2$ groups denote the entity of formula —CONN—CH$_2$—CHOH—CH$_2$—OH.

Thus, preferred structures according to the invention include the compounds of formula (II):

   (IIa)

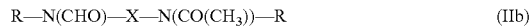   (IIb)

   (IIc)

Formula (II)

In formula (II), each group R has the meaning above, more preferably both iodophenyl groups R are the same and the R$^2$ groups all denote non-ionic hydrophilic moieties, and preferably the R$^2$ groups are linked to iodinated phenyl moiety by amide linkages. X preferably denotes straight chain alkylene groups with 3 to 5 carbon atoms and having one to three hydroxyl substituents at positions that are not adjacent to the nitrogen function.

Compounds of formula (IIa) are particularly preferred, in particular compounds having a monohydroxylated alkylene bridge X, in particularly a propylene bridge.

Some preferred examples the structures according to the invention include the compounds of formulas (III a) to (III u) below.

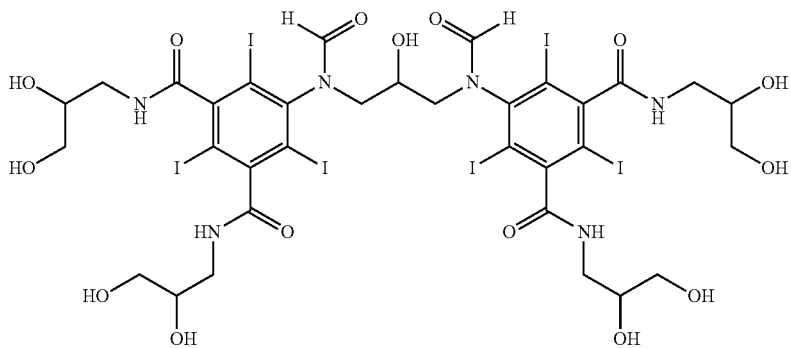

Formula (IIIa)

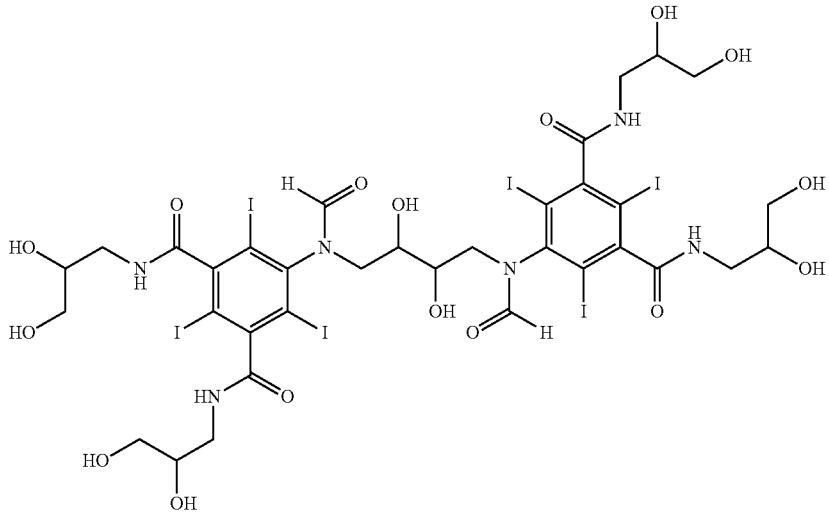

Formula (IIIb)

-continued
Formula (IIIc)
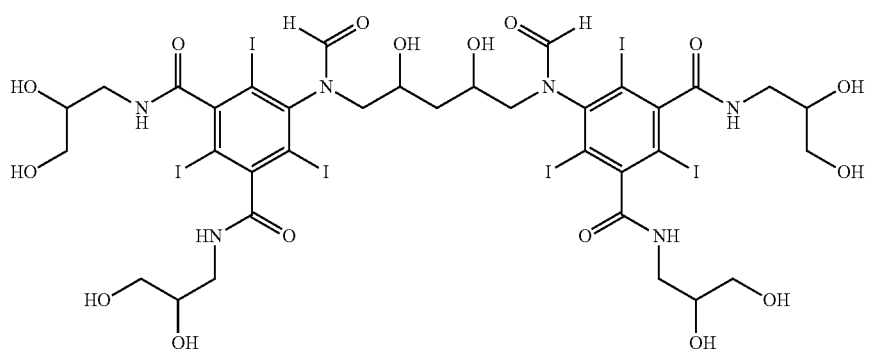
Formula (IIId)
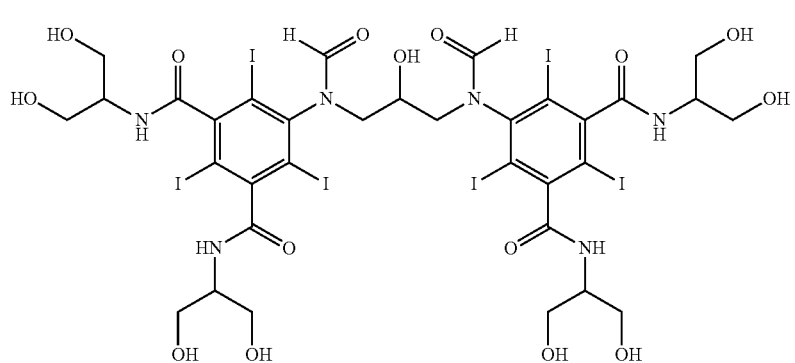
Formula (IIIe)
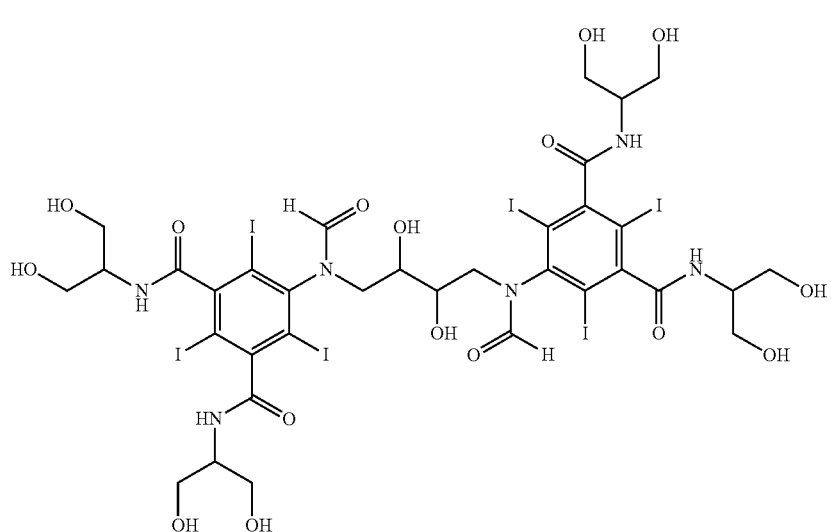
Formula (IIIf)
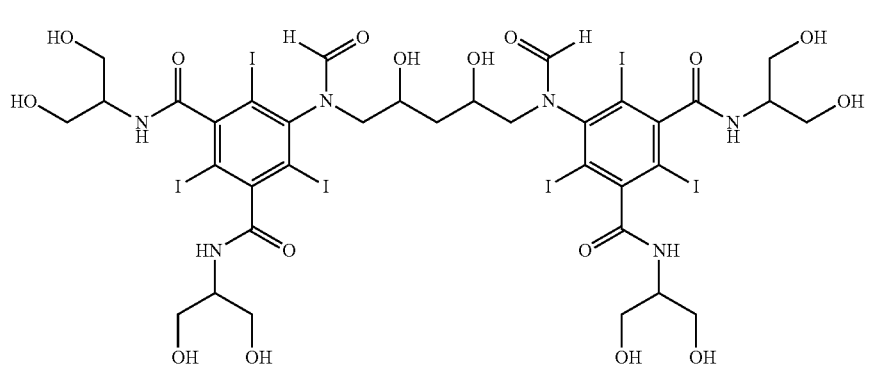

Formula (IIIg)
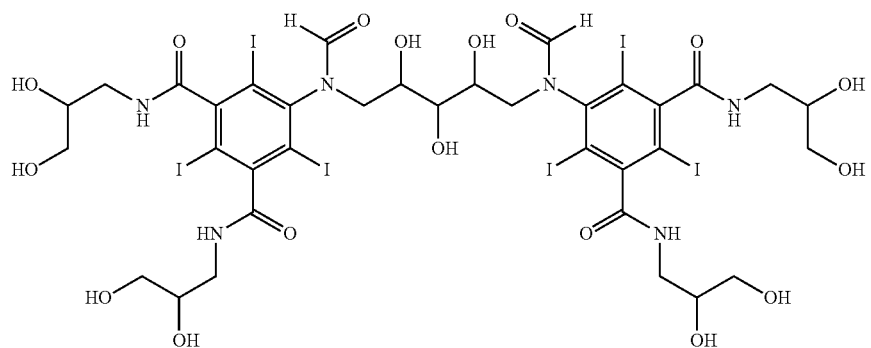
Formula (IIIh)
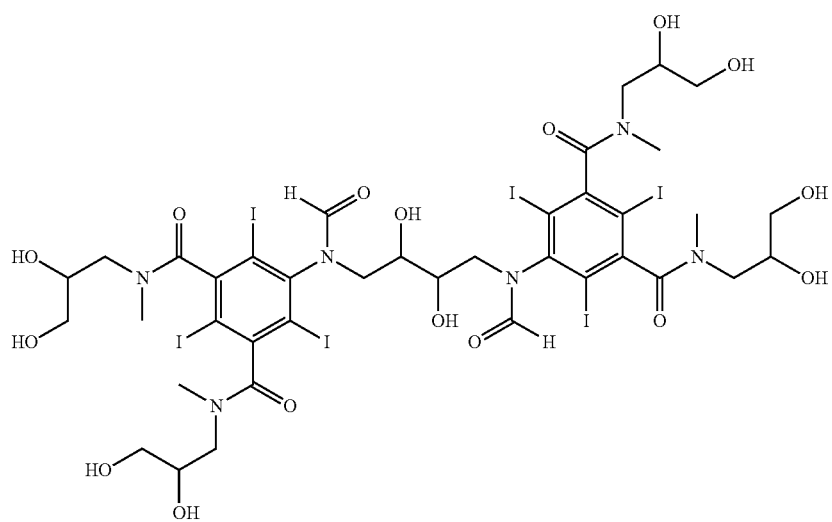
Formula (IIIi)
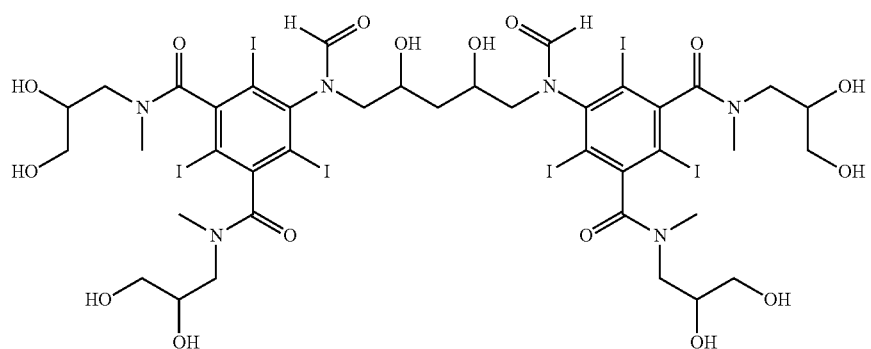
Formula (IIIj)
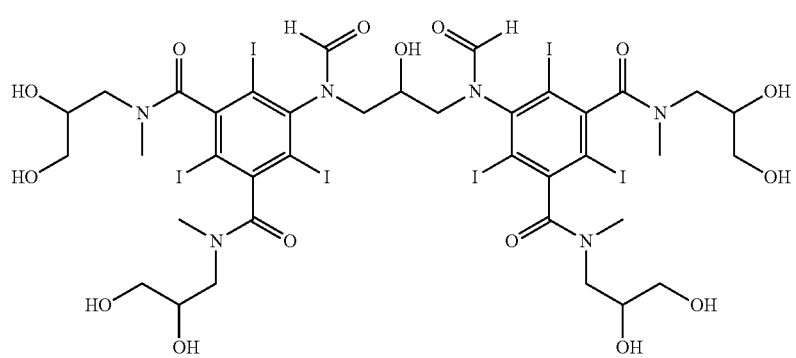

-continued
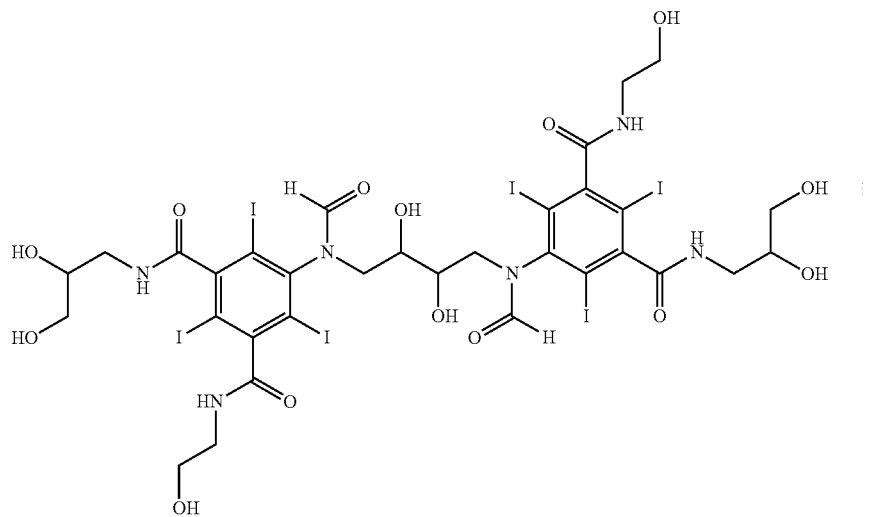
Formula (IIIk)
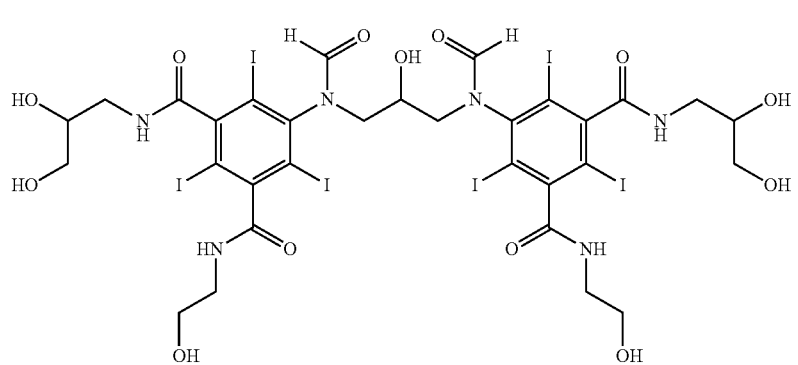
Formula (IIIl)
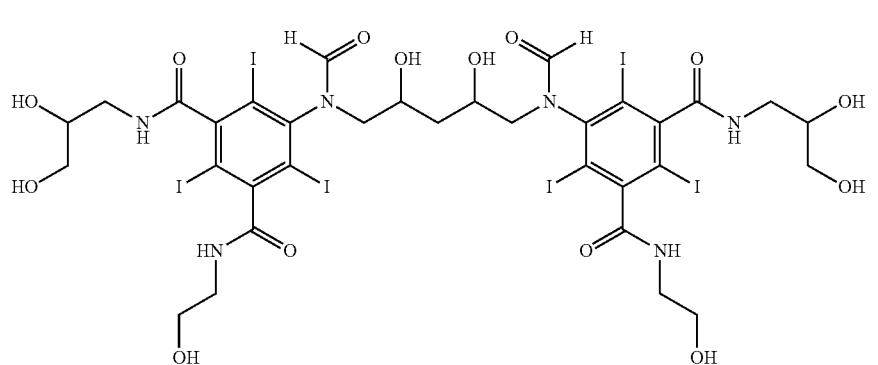
Formula (IIIm)
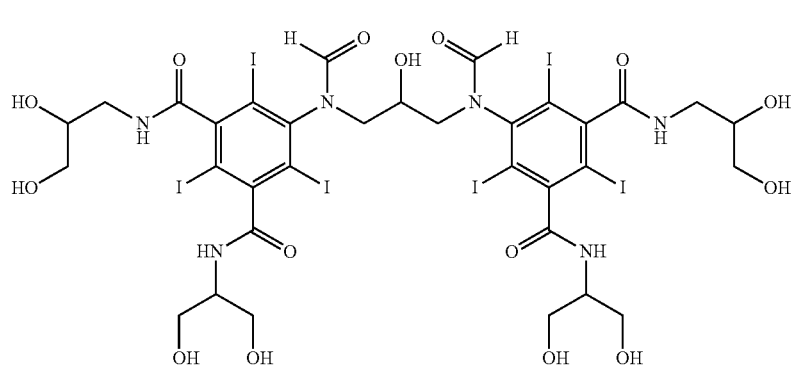
Formula (IIIn)

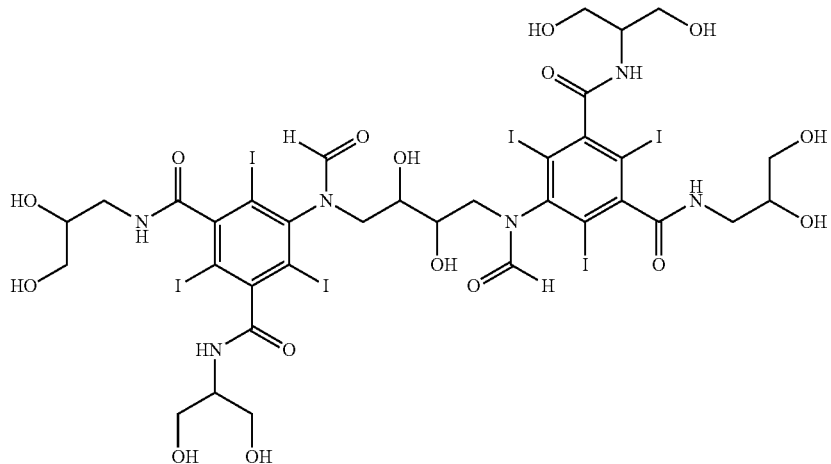
Formula (IIIo)
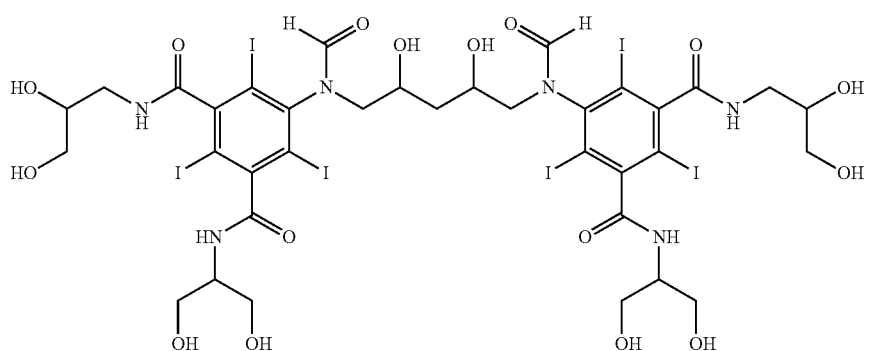
Formula (IIIp)
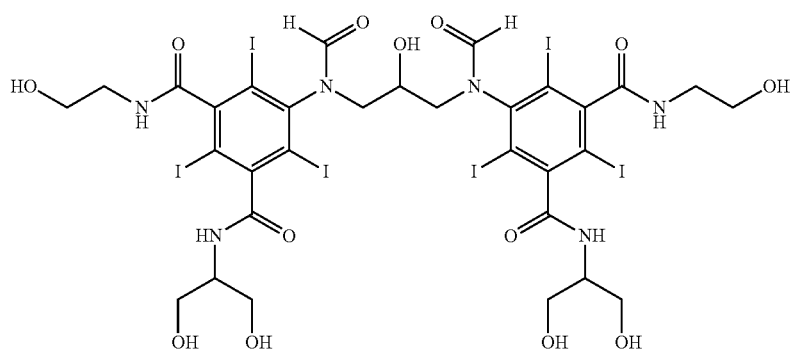
Formula (IIIq)
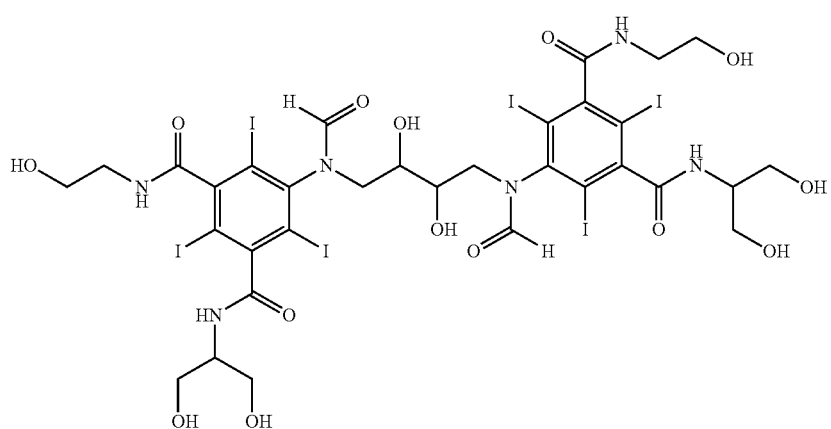
Formula (IIIr)

-continued

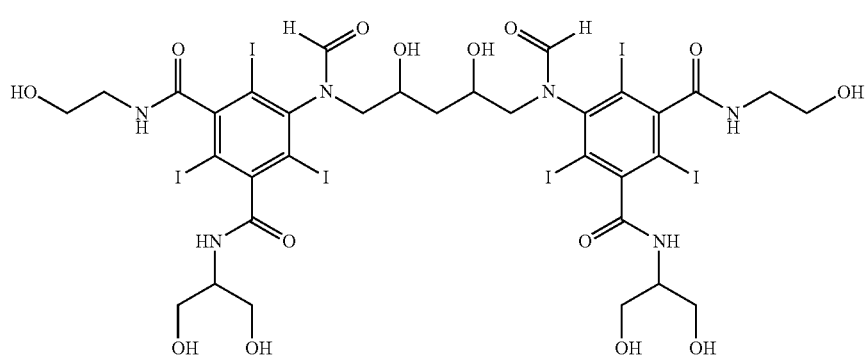

Formula (IIIs)

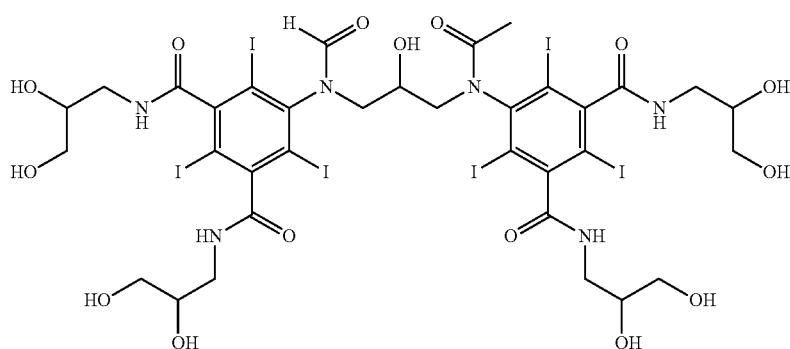

Formula (IIIt)

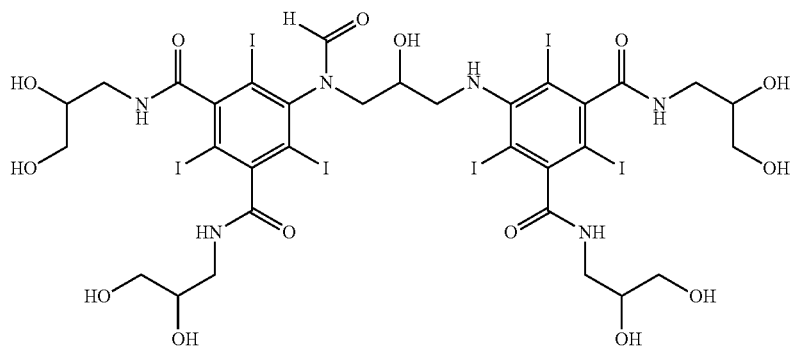

Formula (IIIu)

At an iodine concentration of 320 mg/ml, which is a common concentration for commercially available iodinated contrast media, the concentration of the compound of formula (I) will be approximately 0.42 M (Molar). The contrast medium will be hypoosmolar at this iodine concentration, and this is an advantageous property with regards to the nephrotoxicity of the contrast medium. It is possible to add electrolytes to the contrast medium to lower the cardiovascular effects as explained in WO 90/01194 and WO 91/13636.

Compounds of formula (I) also comprises optical active isomers and will exist in several isomeric forms due to chiral carbon atoms. In addition, the compounds exhibit exo/endo isomerism due to the restricted rotation of the N—CO bond in the formyl function caused by the proximity of the bulk iodine atom. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg H$_2$O, preferably below 850 mOsm/kg H$_2$O and more preferably about 300 mOsm/kg H$_2$O.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

The contrast media containing compounds of formula (I) can be administered by injection or infusion, e.g. by intervascular administration. Alternatively, contrast media containing compounds of formula (I) may also be administered orally. For oral administration the contrast medium may be in the form of a capsule, tablet or as liquid solution.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

The compounds of the general formula (I) can be synthesized by multistep procedures from starting materials that are either known from the state of art or that are commercially available or can readily be produced from commercially available materials. The known synthesis for the production of iodixanol can generally be adapted to produce compounds of formula (I).

Preparation

General procedure for preparation of compounds of formula (I)

Compounds of formula (IVa) and if necessary of formula (IVb)

 Formula (IVa)

 Formula (IVb)

are reacted with a reactive linker group of formula (V)

 Formula (V)

wherein Y and Y' are readily eliminatable atoms or groups and X has the above meaning or a hydroxyl protected derivative thereof or a corresponding epoxide in which one or both of the substituents Y and Y' are replaced by —O—, and if required followed by removal of protecting groups. The groups Y and Y' may be chosen from halogen atoms, e.g. chloride, bromine or iodine, or sulphate hydrocarbylsulphonyloxy groups, e.g. alkyl- or aryl-sulphonyloxy groups such as tosyloxy or mesyloxy Examples of suitable compounds of formula (V) are compounds of formulas (Va), (Vb), (Vc) and (Vd).

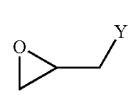 Formula (Va)

wherein Y is a readily eliminatable atom or group.

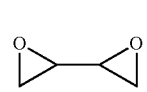 Formula (Vb)

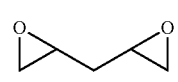 Formula (Vc)

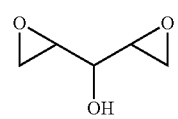 Formula (Vd)

Further, compounds of formula (V) providing a bridge with 3 carbon atoms are described in Bjørsvik, H-R., and Priebe, H. Acta Chem. Scand. 49 (1995) 446-456, "Multivariate data analysis of molecular descriptors estimated by using semi-empirical quantum chemistry methods. Principal properties for synthetic screening of 2-chloromethyl-oxirane and analogues bis-alkylating C3 moieties".

Suitable compounds of formula (V) may thus be epichlorohydrin, butadiene diepoxide, 1,4-pentadiene diepoxide, di(oxiran-2-yl)methanol or any precursor that can form epoxide or diepoxide under basic conditions like 1,4-dichloro-butane-2,3-diol or 1,5-dichloropentane-2,4-diol.

The hydroxyl groups present in the R groups and in the X group may, if desired, be in a hydroxyl protected form. Suitable protecting groups include acyl groups such as acetyl or, where adjacent hydroxyl groups are present, as cyclic ketal or acetal groups.

The reaction between compounds of formulas (IVa) and (V) and optionally between formulas (IVa), (IVb) and (V) is preferably effected in the presence of an acid binding agent, for example an organic or inorganic base preferably in aqueous or alcoholic medium or mixtures thereof such as water and/or an alkanol or glycol; an alkali metal alkoxide such as sodium metoxide or an alkali metal hydroxide such as sodium and potassium hydroxide may be used as base.

Any protecting group may be removed by standard methods, for example by hydrolysis. The compounds of formula (IVa) and (IVb) may be prepared by formylation of the corresponding compounds having free amino groups. In this reaction, hydroxyl groups in the substituents R may also be protected by acylation.

The compounds of formula (I) may be purified in any convenient manner, e.g. by preparative chromatography or by recrystallisation.

Preparation of Intermediates (When not Commercially Available)

The precursors to the compounds of formulas (IVa) and (IVb), the tri-iodinated phenyl groups having a free amino group are commercially available or can be produced following procedures described or referred to e.g. in WO95/35122 and WO98/52911. 5-amino-2,4,6-triiodo-isophtalic acid for example is available e.g. from Aldrich and 5-amino-2,4,6-triiodo-N,N'-bis(2,3-dihydroxypropyl)-isophtalamide is commercially available e.g. from Fuji Chemical Industries, Ltd.

Examples of commercial available precursors of the compounds of formulas (IVa) and (IVb), either commercially available or previously described in the literature include:

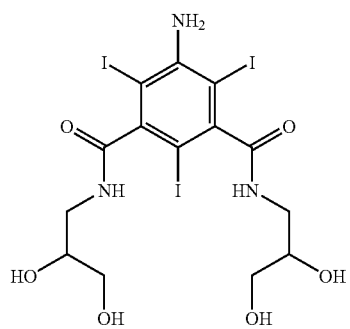 [SMILES: Nc1c(I)c(C(=O)NCC(O)CO)c(I)c(C(=O)NCC(O)CO)c1I]

5-Amino-N,N'-bis-(2,3-dihydroxy-propyl)-2,4,6-triiodo-isophthalamide

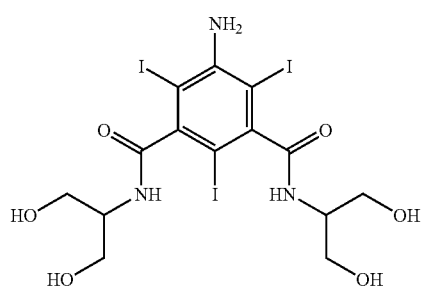 [SMILES: Nc1c(I)c(C(=O)NC(CO)CO)c(I)c(C(=O)NC(CO)CO)c1I]

5-Amino-N-(2,3-dihydroxy-propyl)-N'-(2-hydroxy-1-hydroxymethyl-ethyl)-2,4,6-triiodo-isophthalamide (WO2002044125)

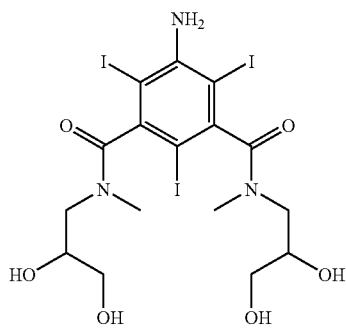 [SMILES: CN(CC(O)CO)C(=O)c1c(I)c(N)c(I)c(C(=O)N(C)CC(O)CO)c1I]

5-Amino-N,N'-bis-(2,3-dihydroxy-propyl)-2,4,6-triiodo-N,N'-dimethyl-isophthalamide

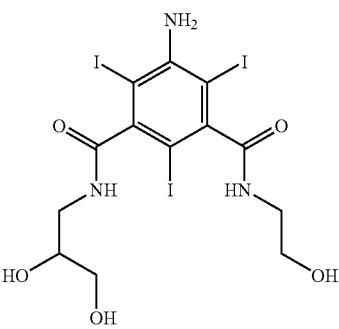 [SMILES: Nc1c(I)c(C(=O)NCCO)c(I)c(C(=O)NCC(O)CO)c1I]

5-Amino-N-(2,3-dihydroxy-propyl)-N'-(2-hydroxy-ethyl)-2,4,6-triiodo-isophthalamide (WO 8700757)

The compounds of formulas (IVa) and (IVb), may be prepared by acylation of the corresponding compounds having free amino groups. In this reaction, hydroxyl groups in the substituents R may also be protected by acylation.

Acylation may be effected by any convenient method, e.g. by use of activated formic acid such as mixed anhydrides which can prepared by a variety of methods described in the literature.

A convenient method of preparing mixed anhydrides is to add a carboxylic acid anhydride to an excess of formic acid under controlled temperature. It is also possible to make mixed anhydrides by addition of a carboxylic acid chloride to a solution of a formic acid salt. Formyl-mixed anhydrides may include acetyl, isobutyryl, pivaloyl, benzoyl etc.

In the present implementation acetic-formic mixed anhydride is employed. To an excess of cooled pre-prepared acetic-formic mixed anhydride is added a 5-amino-monomer and the mixture is stirred overnight. The mixture is concentrated in vacuo and may be used directly in the alkylation step as described in the experimental section (procedure B) or alternatively the O-acylated groups may be hydrolysed prior to alkylation as described in the experimental section (procedure A). Hydrolysis is conveniently performed in aqueous basic media as exemplified in the experimental section or may alternatively be effected by alcoholysis e.g. as described in WO1997000240.

It is also possible to dissolve the 5-aminomonomer in formic acid and subsequently add the carboxylic acid anhydride but in order to reduce unwanted acylation it is preferred to prepare the mixed anhydride separately and subsequently mix this with the 5-aminomonomer as described above.

EXPERIMENTAL

Example 1

5,5'-(2-hydroxypropane-1,3-diyl)bis(formylazanediyl)bis($N^1$,$N^3$-bis(2,3-dihydroxypropyl)-2,4,6-triiodoisophthalamide)

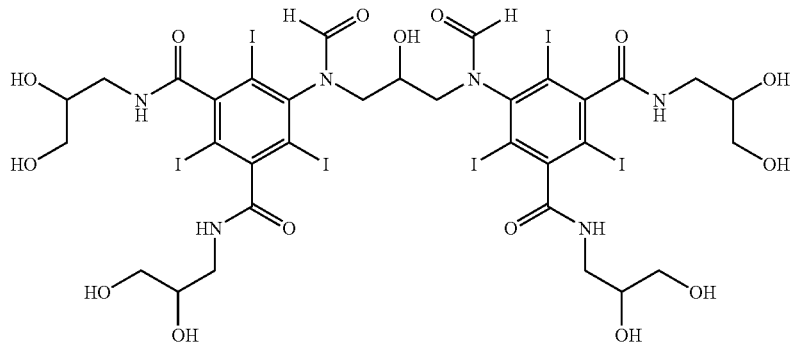

Procedure A:

1a) N,N'-Bis-(2,3-dihydroxy-propyl)-5-formylamino-2,4,6-triiodo-isophthalamide Formic acid (300 ml) was charged in a dry 1000 ml flask fitted with a dropping funnel, stir bar, thermometer and a gas inlet. The acid was cooled on an ice bath under a nitrogen blanket and acetic anhydride (144.8 g, 1.418 mol) was added drop wise at a rate so that the temperature did not exceed 2.5 C. After complete addition, the ice bath was removed and the temperature was allowed to reach 10° C. The mixture was again ice cooled and 5-amino-N,N'-bis(2,3-dihydroxypropyl)-2,4,6-triiodo-isophthalamide (100 g, 141.8 mmol) was added over 5 minutes and the mixture was left stirring over night while attaining ambient temperature. The mixture was evaporated to dryness and methanol (300 ml) and water (300 ml) was added. 2 M potassium hydroxide was added until all material was in solution and a stable pH 12.5 was attained. The methanol was removed in vacuo. The mixture was neutralized with 4 M HCl and a slow precipitation started. 300 ml water was added and the product was precipitated over night.

The precipitate was collected and rinsed with a small amount of water and dried on filter to a moist cake and further dried in vacuo to yield 84.8 g (81.5%) of N,N'-bis-(2,3-dihydroxy-propyl)-5-formylamino-2,4,6-triiodo-isophthalamide.

$^1$H-NMR 500 MHz (solvent: $D_2O$, ref. $H_2O$=4.8 ppm, 25° C.): 8.35 and 8.05 ppm (2s, 1H), 3.94 ppm (m, 2H), 3.67 ppm (m, 2H), 3.55 ppm (m, 2H), 3.45 ppm (m, 2H), 3.34 ppm (m, 2H).

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave two peaks centred at 5.5 minutes with m/z (M+H+) 733.828, m/z (M+$NH_4$+) 750.855, m/z (M+Na+) 755.817 corresponding to the structure.

1b) 5,5'-(2-hydroxypropane-1,3-diyl)bis(formylazanediyl)bis($N^1$,$N^3$-bis(2,3-dihydroxypropyl)-2,4,6-triiodoisophthalamide)

Potassium hydroxide (1.07 g) was dissolved in water (6.9 ml) and methanol (3.4 ml) in a 50 ml round bottomed flask fitted with a magnetic stir bar. Boric acid (0.41 g, 6.6 mmol) and N,N'-bis-(2,3-dihydroxy-propyl)-5-formylamino-2,4,6-triiodo-isophthalamide (7.0 g, 9.56 mmol) was added to the stirred solution. Epichlorohydrin (260 ul, 3.32 mmol) was added to the solution and a pH electrode was fitted in the flask and the pH was maintained at pH 12.7 by drop wise addition of 4 M potassium hydroxide for 4 h. At this point, the mixture was left stirring over night. The pH was adjusted with 4 M hydrochloric acid to pH 4 and the methanol was removed in vacuo. The remaining aqueous solution was diluted with water (75 ml) and treated with ion exchangers (AMB200C and IRA67) to zero conductivity. The ion exchangers were removed by filtration and rinsed with water and the combined aqueous filtrates were freeze dried. The crude product was purified by preparative HPLC (column Phenomenex Luna C18 10 μm solvents: A=water and B=acetonitrile; gradient 05-20% B over 60 min. After freeze drying 3.80 g of 5,5'-(2-hydroxypropane-1,3-diyl)bis(formylazanediyl)bis($N^1$,$N^3$-bis(2,3-dihydroxypropyl)-2,4,6-triiodoisophthalamide) (74.8% yield) was obtained.

$^1$H-NMR 500 MHz (solvent: $D_2O$, ref. $H_2O$=4.8 ppm, 25° C.): 8.34 and 8.08 ppm (m, 2 H), 2.80-4.80 ppm (m 26 H).

LC-MS TOF; 1522.68 m/z (M+H$^+$), 1544.66 m/z (M+Na$^+$).

Example 2

5,5'-(2-hydroxypropane-1,3-diyl)bis(formylazanediyl)bis($N^1,N^3$-bis(2,3-dihydroxypropyl)-2,4,6-triiodoisophthalamide)

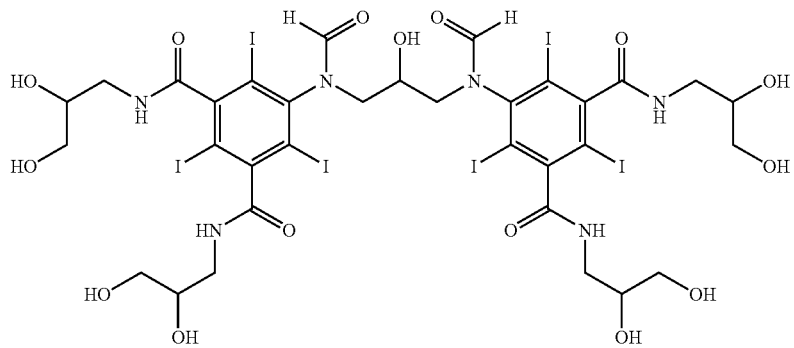

Procedure B:

2a) 1-formylamino-3,5-bis(2,3-bis(formyloxy)propan-1-ylcarbamoyl)-2,4,6-triiodo-benzene Formic acid (4 L) was charged in a dry 5000 ml jacketed reactor on cryostat was fitted with a dropping funnel, mechanical stirring, thermometer and a gas inlet. The acid was cooled with a cryostat under a nitrogen blanket. Acetic anhydride (1.98 L, 21.0 mol) was added drop wise at a rate so that the temperature did not exceed 12.0° C. After 7.5 h the addition was completed and the mixture was cooled to 3.8° C. and 5-amino-N,N'-bis(2,3-dihydroxypropyl)-2,4,6-triiodo-isophthalamide (1.481 kg, 2.1 mol) was added over 20 minutes and the mixture was left stirring over night attaining ambient temperature.

The reaction mixture was evaporated in vacuo at 40° C. to a moist mass, this was further dried in a vacuum oven at 40° C. to yield 1754 g (98.8%) of 1-formylamino-3,5-bis(2,3-bis(formyloxy)propan-1-ylcarbamoyl)-2,4,6-triiodo-benzene. The product was used in the next step without purification.

The obtained product does contain some minor fraction of O-acetyl esters, as the product is used directly in the next step without purification this can be disregarded.

2b) 5,5'-(2-hydroxypropane-1,3-diyl)bis(formylazanediyl)bis($N^1,N^3$-bis(2,3-dihydroxypropyl)-2,4,6-triiodoisophthalamide)

A 1000 ml jacketed reactor on cryostat was fitted with internal pH electrode, thermometer and stirrer. The reactor was cooled to 10° C., water (77 ml), methanol (154 ml) and boric acid (49.7 g, 803.5 mmol) were charged in the reactor. A slow addition of potassium hydroxide (9 M) was started and at T=0 finely crushed 1-formylamino-3,5-bis(2,3-bis(formyloxy)propan-1-ylcarbamoyl)-2,4,6-triiodo-benzene (341.5 g, 401.8 mmol) was added to the reactor. The addition rate of potassium hydroxide was adjusted to keep the pH within pH 11.6-11.7 and the temperature was maintained at 10° C.±1. At T=105 minutes the starting material was largely in solution and epichlorohydrin (16.07 ml, 204.9 mmol) was added in 5 portions over 60 minutes. The pH was maintained within pH 11.6-11.7 by continuous addition of potassium hydroxide (9 M).

At T=465 minutes the pH was 11.7 and the mixture was left stirring over night at 10° C. without pH-adjustment. The following day the pH was maintained within pH 11.6-11.7 with continuous addition of potassium hydroxide (9 M). At the end of the day a temperature gradient of 1° C./h to 20° C. was started and the mixture was left stirring over the night. The following day the reaction mixture was diluted with water (500 ml) and taken out of the reactor and treated with acidic ion exchanger AMB200C (1841 ml, 3093.6 mmol). The pH was now pH 1.38. After 5 minutes basic ion exchanger IRA67 (2946 ml, 3093.6 mmol) was added and the pH gradually attained pH 5.67. After 4 h the ion exchangers were removed by filtration and rinsed with water (4×2 liters).

HPLC analysis (UV 254 nm) showed the product to be present in a purity of 90.4%. The combined aqueous filtrates were combined and reduced to 1.5 liters in vacuo at 40° C.

The crude product was purified by preparative HPLC (column Phenomenex Luna C18 (2) 10 µm solvents: A=water and B=acetonitrile; gradient 05-20% B over 60 min. After freeze drying 222.8 g 5,5'-(2-hydroxypropane-1,3-diyl)bis(formylazanediyl)bis($N^1,N^3$-bis(2,3-dihydroxypropyl)-2,4,6-triiodoisophthalamide) (72.9% yield) was obtained.

LC-MS TOF 1522.68 m/z (M+H$^+$), 1544.66 m/z (M+Na$^+$).

$^1$H-NMR 500 MHz (solvent: D$_2$O, ref. H$_2$O=4.8 ppm, 25° C.): 8.34 and 8.08 ppm (m, 2 H), 2.80-4.80 ppm (m 25 H).

Example 3

5,5'-(2,3-dihydroxybutane-1,4-diyl)bis(formylazanediyl)bis(N¹, N³-bis(2,3-dihydroxypropyl)-2,4,6-triiodoisophthalamide)

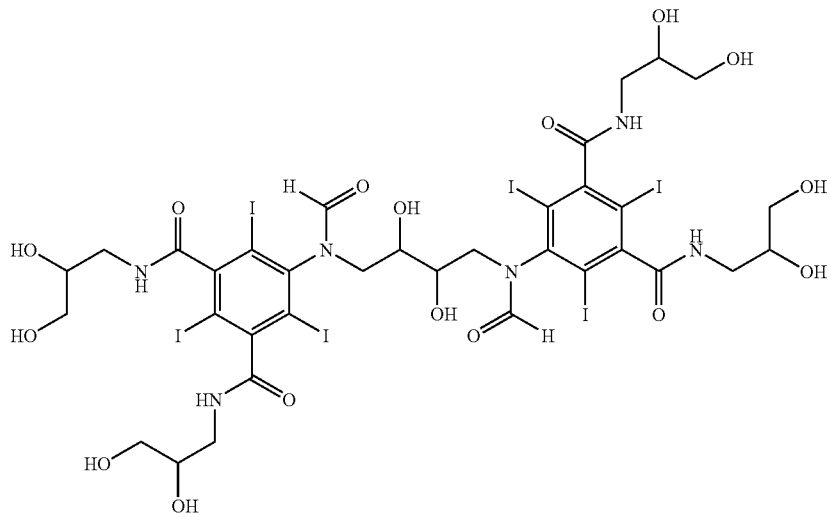 [SMILES: O=CN(CC(O)C(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water (10 ml), methanol (5 ml) and potassium hydroxide (1.0 g, 16.4 mmol) was added $N^1,N^3$-bis(2,3-dihydroxypropyl)-5-formylamino-2,4,6-triiodo-isophthalamide (Example 1a) (10.0 g, 13.6 mmol). To the clear solution was then added boric acid (0.59 g, 9.5 mmol). The pH was continuously maintained at pH 12.6 by addition of potassium hydroxide (10 M) and 1,3-butadiene diepoxide (0.40 g, 4.7 mmol) was added. The pH of the solution was continuously maintained within the interval from 12.6 to 13 by addition of solid boric acid for 5 hours and then left over the weekend. The solution was neutralized by addition of hydrochloric acid (18% w) and then treated with ion exchangers (AMB200C, 20 ml) and (IRA67, 20 ml). The resins were removed by filtration and rinsed with water and the combined aqueous volume was reduced in vacuo. The crude product was purified by preparative HPLC (column Phenomenex Luna C18 10 μm 250×50.0 mm, solvents: A=water and B=acetonitrile; gradient 0-10% B over 60 min; flow 50.0 ml/min, UV detection at 214 nm and 254 nm). After freeze drying 3.1 g 5.5'-(2,3-dihydroxybutane-1,4-diyl)bis(formylazanediyl)bis($N^1,N^3$-bis(2,3-dihydroxypropyl)-2,4,6-triiodo-isophthalamide) (43% yield) was obtained.

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave four peaks centred at 8.6 minutes with m/z 1552.5 [M+H]+ corresponding to the structure.

$^1$H-NMR 500 MHz (solvent: $D_2O$, ref. $H_2O$=4.8 ppm, 25° C.): 8.48 ppm (m, 1H), 8.25 ppm (m, 1H) 3.40-4.40 ppm (m, 26H).

Example 4

5,5'-(2,4-dihydroxypentane-1,5-diyl)bis(formylazanediyl)bis($N^1,N^3$-bis(2,3-dihydroxypropyl)-2,4,6-triiodoisophthalamide)

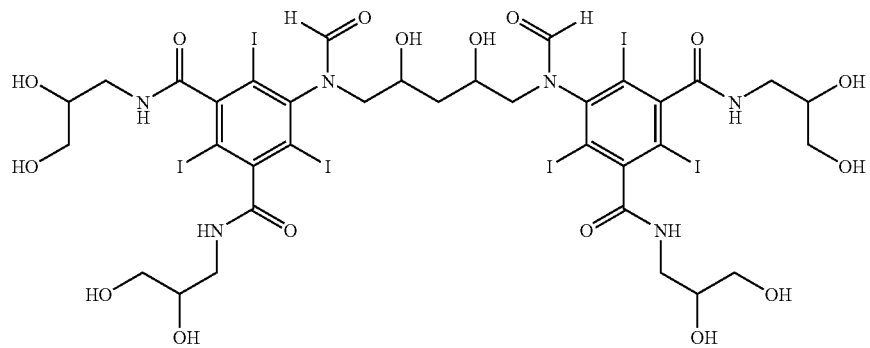 [SMILES: O=CN(CC(O)CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water (10 ml), methanol (5 ml) and potassium hydroxide (1.0 g, 16.4 mmol) was added $N^1,N^3$-bis(2,3-dihydroxypropyl)-5-formylamino-2,4,6-triiodo-isophthalamide (Example 1a) (10.0 g, 13.6 mmol). To the clear solution was added boric acid (0.59 g, 9.5 mmol). The pH was continuously maintained at pH 12.6 by addition of potassium hydroxide (10 M) and 1,4-Pentadiene diepoxide (0.47 g, 4.7 mmol) was added. The pH of the solution was continuously maintained within the interval from 12.6 to 13 by addition of solid boric acid. The reaction was stirred over the weekend and then neutralized by addition of hydrochloric acid (18% w) and then treated with ion exchangers (AMB200C, 20 ml) and (IRA67, 20 ml). The resins were removed by filtration and rinsed with water and the combined aqueous volume was reduced in vacuo. The crude product was purified by preparative HPLC (column Phenomenex Luna C18 10 μm 250×50.0 mm, solvents: A=water and B=acetonitrile; gradient 0-17% B over 60 min; flow 50.0 ml/min, UV detection at 214 nm and 254 nm). After freeze drying 1.98 g 5,5'-(2,4-dihydroxypentane-1,5-diyl)bis(formylazanediyl)bis($N^1,N^3$-bis(2,3-dihydroxypropyl)-2,4,6-triiodoisophthalamide) (27% yield) was obtained.

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave four peaks centered at 10 minutes with m/z 1566.5 [M+H]$^+$ consistent with the expected product mass.

$^1$H-NMR 500 MHz (solvent: D$_2$O, ref. H$_2$O=4.8 ppm, 25° C.): 8.15 ppm (m, 1H), 8.10 ppm (m, 1H), 2.90-4.15 ppm (m, 26H) 1.42-1.85 (m, 2H).

Example 5

5,5'-(2,3,4-trihydroxypentane-1,5-diyl)bis(formylazanediyl)bis($N^1,N^3$-bis(2,3-dihydroxypropyl)-2,4,6-triiodoisophthalamide)

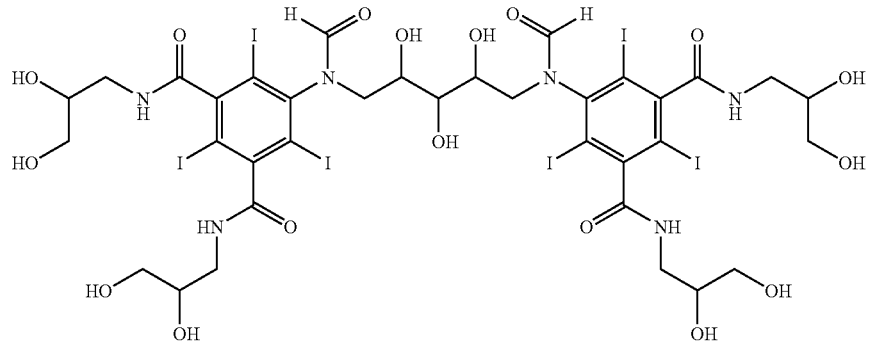 [SMILES: O=CN(CC(O)C(O)C(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water (10 ml), methanol (5 ml) and potassium hydroxide (1.0 g, 16.4 mmol) was added $N^1,N^3$-bis(2,3-dihydroxypropyl)-5-formylamino-2,4,6-triiodo-isophthalamide (Example 1a) (10.0 g, 13.6 mmol). To the clear solution was added boric acid (0.59 g, 9.5 mmol). The pH was continuously maintained at pH 12.6 by addition of potassium hydroxide (10 M) and 1,4-pentadien-3-ol diepoxide (0.55 g, 4.7 mmol) was added. The pH interval of the solution was maintained between pH 12.6-13 by addition of solid boric acid. The reaction was left stirring over the weekend and then neutralized with hydrochloric acid (18% w) and treated with ion exchangers (AMB200C, 20 ml) and (IRA67, 20 ml). The resins were filtered off and rinsed with water and the combined aqueous solution was reduced in vacuo. The crude product was purified by preparative HPLC (column Phenomenex Luna C18 10 μm 250×50.0 mm, solvents: A=water and B=acetonitrile; gradient 0-10% B over 60 min; flow 50.0 ml/min, UV detection at 214 nm and 254 nm). After freeze drying 1.386 g 5,5'-(2,3,4-trihydroxypentane-1,5-diyl)bis(formylazanediyl)bis($N^1,N^3$-bis(2,3-dihydroxypropyl)-2,4,6-triiodoisophthalamide) (19% yield) was obtained.

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave five peaks centered at 8.4 minutes with m/z 1582.5 [M+H]$^+$ consistent with the expected product mass.

$^1$H NMR, 500 MHz (DMSO, 25° C.): 8.6-7.8 ppm (m, 6H), 5.2-4.2 ppm (m, 10H), 4.2-3.18 ppm (m, 21H) 3.15-2.85 (m, 7H).

Example 6

5,5'-(2,3-dihydroxybutane-1,4-diyl)bis(formylazanediyl)bis(N$^1$,N$^3$-bis(2,3-dihydroxypropyl)-2,4,6-triiodo-N$^1$,N$^3$-dimethylisophthalamide)

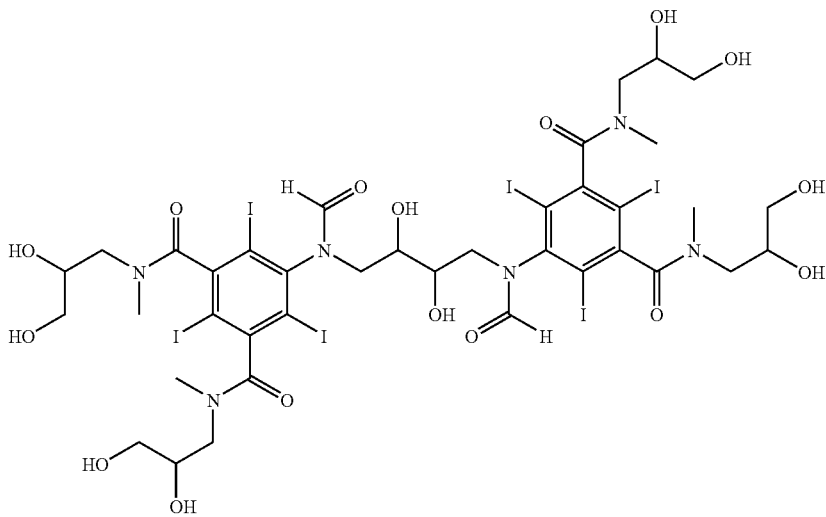 [SMILES: CN(CC(O)CO)C(=O)c1c(I)c(C(=O)N(C)CC(O)CO)c(I)c(N(C=O)CC(O)C(O)CN(C=O)c2c(I)c(C(=O)N(C)CC(O)CO)c(I)c(C(=O)N(C)CC(O)CO)c2I)c1I]

To a stirred solution of 1-formylamino-3,5-bis(2,3-bis(formyloxy)propan-1-yl-methyl-carbamoyl)-2,4,6-triiodobenzene (Example 8a)(9.9 g, 11.3 mmol) in water (10 ml) and methanol (5 ml) was added potassium hydroxide (10 M) to maintain pH at pH 12.6. After 1.5 h, boric acid (0.56 g, 9.0 mmol) was added. The pH was continuously maintained at pH 12.6 by addition of potassium hydroxide (10 M) and 1,3-butadiene diepoxide (0.39 g, 4.5 mmol) was added. The pH was maintained between pH 12.6-13 by addition of solid boric acid and left stirring over night. The solution was neutralized by addition of hydrochloric acid (18%) and treated with ion exchangers (AMB200C, 19 ml) and (IRA67, 19 ml). The resins were filtered off and rinsed with water and the combined aqueous solution was reduced in vacuo. The crude product was purified by preparative HPLC (column Phenomenex Luna C18 10 µm 250×50.0 mm, solvents: A=water and B=acetonitrile; gradient 05-20% B over 60 min; flow 50.0 ml/min). After freeze drying 1.38 g of 5,5'-(2,3-dihydroxybutane-1,4-diyl)bis(formylazanediyl)bis(N$^1$,N$^3$-bis(2,3-dihydroxypropyl)-2,4,6-triiodo-N$^1$,N$^3$-dimethylisophthalamide) (19% yield) was obtained.

Analysis by LC-MS (column Agilent Zorbax SB-Aq 3.5 µm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a multiply split peak at 11.2 minutes with m/z 1608.7 [M+H]+ consistent with the product mass.

$^1$H NMR, 500 MHz (DMSO, 25° C.): 8.35 ppm (bs, 1H), 8.2-8.0 ppm (m, 1.3H), 5.1-4.4 ppm (m, 9.8H), 4.3-3.4 (m, 19H), 3.3-2.7 ppm (m, 19H).

Example 7

5,5'-(2,4-dihydroxypentane-1,5-diyl)bis(formylazanediyl)bis(N$^1$,N$^3$-bis(2,3-dihydroxypropyl)-2,4,6-triiodo-N1,N$^3$-dimethylisophthalamide)

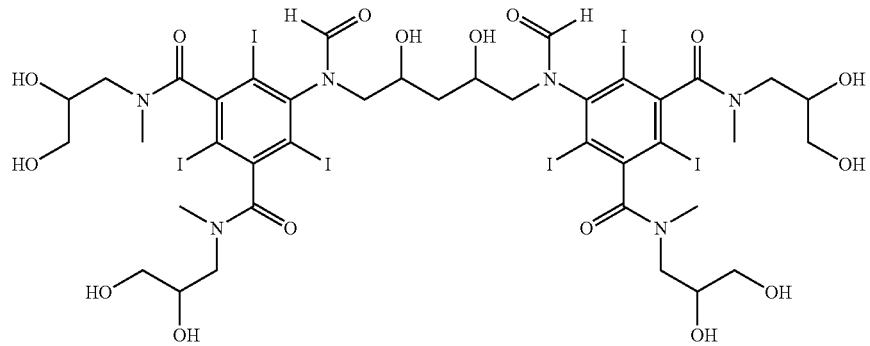 [SMILES: CN(CC(O)CO)C(=O)c1c(I)c(C(=O)N(C)CC(O)CO)c(I)c(N(C=O)CC(O)CC(O)CN(C=O)c2c(I)c(C(=O)N(C)CC(O)CO)c(I)c(C(=O)N(C)CC(O)CO)c2I)c1I]

To a stirred solution of 1-formylamino-3,5-bis(2,3-bis(formyloxy)propan-1-yl-methyl-carbamoyl)-2,4,6-triiodo-benzene (Example 8a)(9.4 g, 10.8 mmol) in water (10 ml) and methanol (5 ml) was added potassium hydroxide (10 M) to maintain pH at pH 12.6. After 30 min, boric acid (0.53 g, 8.6 mmol) was added. The pH was continuously maintained at pH 12.6 by addition of potassium hydroxide (10 M) and 1,4-pentadiene diepoxide (0.43 g, 4.3 mmol) was added. The pH was maintained between pH 12.6-13 by addition of solid boric acid. The reaction was left stirring for 6 days. The solution was neutralized by addition of hydrochloric acid (18%) to pH 7 and treated with ion exchangers (AMB200C, 18 ml) and (IRA67, 18 ml). The resins were filtered off and rinsed with water and the combined aqueous solution was reduced in vacuo. The crude product was purified by preparative HPLC (column Phenomenex Luna C18 10 μm 250×50.0 mm, solvents: A=water and B=acetonitrile; gradient 05-20% B over 60 min; flow 50.0 ml/min). After freeze drying 740 mg 5,5'-(2,4-dihydroxypentane-1,5-diyl)bis(formylazanediyl)bis($N^1$,$N^3$-bis(2,3-dihydroxypropyl)-2,4,6-triiodo-$N^1$,$N^3$-dimethylisophthalamide) (11% yield) was obtained.

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a multiply split peak at 11.5 minutes with m/z 1622.7 [M+H]$^+$ consistent with the product mass.

$^1$H NMR, 500 MHz (DMSO, 25° C.): 8.38 ppm (bs, 0.9H), 8.18-8.0 ppm (m, 1.2H), 5.0-4.3 ppm (m, 9.6H), 4.3-3.4 (m, 18.7H), 4.15-2.7 ppm (m, 19.5H), 2.8-2.4 ppm (2H)

Example 8

5,5'-(2-hydroxypropane-1,3-diyl)bis(formylazanediyl)bis($N^1$,$N^3$-bis(2,3-dihydroxypropyl)-2,4,6-triiodo-$N^1$,$N^3$-dimethylisophthalamide)

8a) 1-formylamino-3,5-bis(2,3-bis(formyloxy)propan-1-yl-methyl-carbamoyl)-2,4,6-triiodo-benzene Formic acid (300 ml) was charged in a dry 1000 ml flask fitted with dropping funnel, stir bar, thermometer and gas inlet. The acid was cooled on an ice bath under a nitrogen blanket and acetic anhydride (128.3 ml, 1.357 mol) was added drop wise over 2 h not allowing the temperature to exceed 4.5 C. After complete addition the temperature was allowed to reach 10° C. and the ice bath was put back. When the mixture was cooled to 3° C. the entire reaction mixture was poured into a flask containing solid 5-amino-N,N'-bis(2,3-dihydroxypropyl)-N,N'-dimethyl-2,4,6-triiodo-isophtalamide (99.5 g, 135.7 mmol). The mixture was left stirring over night. The now homogenous solution was evaporated to dryness in vacuo at 40° C. and used without purification in the next step.

The obtained product does contain some minor fraction of O-acetyl esters, as the product is used directly in the next step without purification this can be disregarded.

8b) 5,5'-(2-hydroxypropane-1,3-diyl)bis(formylazanediyl)bis($N^1$,$N^3$-bis(2,3-dihydroxypropyl)-2,4,6-triiodo-$N^1$,$N^3$-dimethylisophthalamide)

To flask fitted with a flask fitted with pH electrode, stir bar and thermometer was added water (6 ml), methanol (3 ml) water and 1-formylamino-3,5-bis(2,3-bis(formyloxy)propan-1-yl-methyl-carbamoyl)-2,4,6-triiodo-benzene (7.6 g, 10 mmol) followed by addition of Boric acid (1.24 g, 20 mmol). Potassium hydroxide (10 M) was added continuously to maintain a stable pH 11.5 and the temperature was kept at 10° C. with a water/ice bath. When a stable pH 11.5 was reached, epichlorohydrin (527 mg, 5.7 mmol) was added over 15 minutes to the now clear solution. The pH was maintained between pH 12.5-12.8 by addition of solid boric acid at 10° C., after 5 h the mixture was left stirring over night. The reaction mixture was diluted with water (50 ml) and treated with ion exchangers (AMB200C, 15 ml) and (IRA67, 15 ml). The resins were filtered off and rinsed with water and the combined aqueous solution was reduced in vacuo. The crude product was purified by preparative HPLC (column Phenomenex Luna C18 10 μm 250×50.0 mm, solvents: A=water and B=acetonitrile; gradient 05-20% B over 60 min; flow 50.0 ml/min). After freeze drying 2.40 g 5,5'-(2-hydroxypropane-1,3-diyl)bis(formylazanediyl)bis($N^1$,$N^3$-bis(2,3-dihydroxypropyl)-2,4,6-triiodo-$N^1$,$N^3$-dimethylisophthalamide) (30% yield) was obtained.

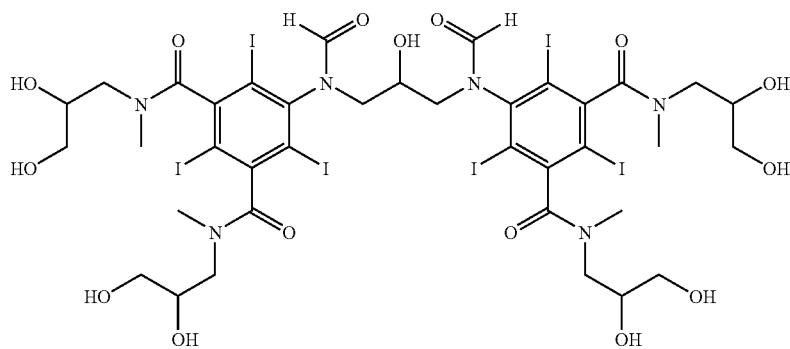 [SMILES: CN(CC(O)CO)C(=O)c1c(I)c(C(=O)N(C)CC(O)CO)c(I)c(N(C=O)CC(O)CN(C=O)c2c(I)c(C(=O)N(C)CC(O)CO)c(I)c(C(=O)N(C)CC(O)CO)c2I)c1I]

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a broad peak at 11.9 minutes with m/z 1578.7 [M+H]+ consistent with the product mass.

$^1$H NMR, 500 MHz (DMSO, 25° C.): 8.50-7.95 ppm (m, 2H), 5.1-3.4 ppm (m, 27.6H), 3.3-2.7 ppm (m, 18.4H).

Example 9

5,5'-(2-hydroxypropane-1,3-diyl)bis(formylazanediyl)bis(N¹,N³-bis(1,3-dihydroxypropan-2-yl)-2,4,6-triiodoisophthalamide)

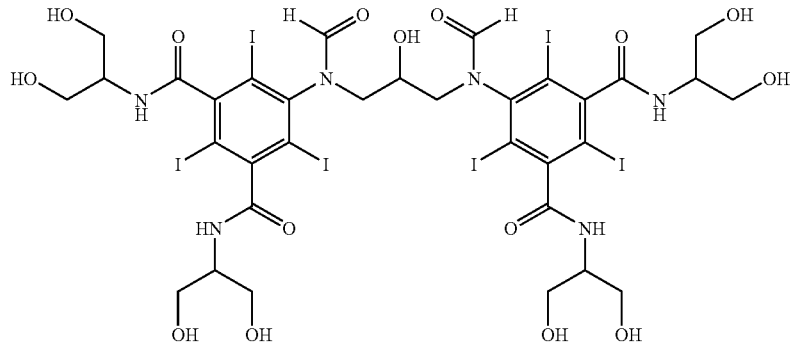 [SMILES: O=CN(CC(O)CN(C=O)c1c(I)c(C(=O)NC(CO)CO)c(I)c(C(=O)NC(CO)CO)c1I)c1c(I)c(C(=O)NC(CO)CO)c(I)c(C(=O)NC(CO)CO)c1I]

9a) 1-formamido-3,5-bis(1,3-bis(formyloxy)propan-2-ylcarbamoyl)-2,4,6-triiodo-benzene Formic acid (800 ml) was charged in a dry 2000 ml flask fitted with dropping funnel, stir bar, thermometer and gas inlet. The acid was cooled on an ice bath under a nitrogen blanket and acetic anhydride (436 ml, 3.972 mol) was added drop wise over 2 h not allowing the temperature to exceed 4.5° C. After complete addition the temperature was allowed to reach 10° C. and the ice bath was put back. When the mixture was cooled to 3° C., 5-amino-N¹,N³-bis(1,3-dihydroxypropan-2-yl)-2,4,6-triiodoisophthalamide (280.0 g, 397.2 mmol) was added and the mixture was left stirring over night. The now homogenous solution was evaporated to dryness in vacuo at 40° C. and used without purification in the next step.

The obtained product does contain some minor fraction of O-acetyl esters, as the product is used directly in the next step without purification this can be disregarded.

9b) 5,5'-(2-hydroxypropane-1,3-diyl)bis(formylazanediyl)bis(N¹,N³-bis(1,3-dihydroxypropan-2-yl)-2,4,6-triiodoisophthalamide)

To a stirred slurry of 1-formamido-3,5-bis(1,3-bis(formyloxy)propan-2-ylcarbamoyl)-2,4,6-triiodo-benzene (11.5 g, 13.6 mmol) in water (5 ml) and methanol (5 ml) was added boric acid (0.60 g, 9.6 mmol). A potassium hydroxide solution (10 M)) was then added drop wise to maintain the pH at pH 12.6. To the clear solution was added epichlorohydrin (0.44 g, 4.8 mmol). The pH was maintained between pH 12.6-13 by addition of solid boric acid. The reaction was left stirring over night and then neutralized by addition of hydrochloric acid (18%) and treated with ion exchangers (AMB200C, 36 ml) and (IRA67, 34 ml). The resins were filtered off and rinsed with water and the combined aqueous solution was reduced in vacuo. The product was purified by preparative HPLC (column Phenomenex Luna C18 10 µm 250×50.0 mm, solvents: A=water and B=acetonitrile; gradient 05-20% B over 60 min; flow 50.0 ml/min). After freeze drying 2.9 g 5,5'-(2-hydroxypropane-1,3-diyl)bis(formylazanediyl)bis(N¹,N³-bis(1,3-dihydroxypropan-2-yl)-2,4,6-triiodoisophthalamide) (40% yield) was obtained.

LC-MS (column Agilent Zorbax SB-Aq 3.5 µm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave three peaks centred at 9.3 minutes with m/z 1522.6 [M+H]+ consistent with the expected product mass.

¹H NMR, 500 MHz (DMSO, 25° C.): 8.5-7.4 ppm (m, 6H), 5.2-4.4 ppm (m, 9.4H), 4.4-3.4 ppm (m, 24H), 3.25-3.15 ppm (m, 0.5H).

Example 10

5,5'-(2,3-dihydroxybutane-1,4-diyl)bis(formylazanediyl)bis(N¹,N³-bis(1,3-dihydroxypropan-2-yl)-2,4,6-triiodoisophthalamide)

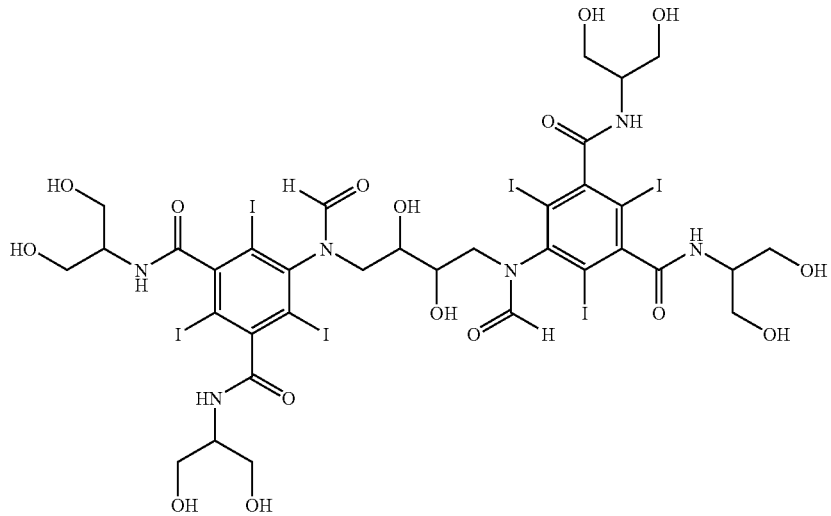 [SMILES: O=CN(CC(O)C(O)CN(C=O)c1c(I)c(C(=O)NC(CO)CO)c(I)c(C(=O)NC(CO)CO)c1I)c1c(I)c(C(=O)NC(CO)CO)c(I)c(C(=O)NC(CO)CO)c1I]

To a stirred slurry of 1-formamido-3,5-bis(1,3-bis(formyloxy)propan-2-ylcarbamoyl)-2,4,6-triiodo-benzene (Example 9a) (11.5 g, 13.6 mmol) in water (5 ml) and methanol (5 ml) was added solid boric acid (0.60 g, 9.6 mmol). A potassium hydroxide solution (10 M)) was then added drop wise to maintain the pH at pH 12.6. To the clear solution was added 1,3-butadiene diepoxide (0.41 g, 4.8 mmol). The pH was maintained between pH 12.6-13 by addition of solid boric acid. The reaction was left stirring over night and then neutralized by addition of hydrochloric acid (18%) and treated with ion exchangers (AMB200C, 36 ml) and (IRA67, 36 ml). The resins were filtered off and rinsed with water and the combined aqueous solution was reduced in vacuo. The product was purified by preparative HPLC (column Phenomenex Luna C18 10 μm 250×50.0 mm, solvents: A=water and B=acetonitrile; gradient 0-20% B over 60 min; flow 50.0 ml/min) After freeze drying 3.1 g 5,5'-(2,3-dihydroxybutane-1,4-diyl)bis(formylazanediyl)bis($N^1,N^3$-bis(1,3-dihydroxypropan-2-yl)-2,4,6-triiodoisophthalamide) was obtained (42% yield).

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave three peaks centred at 8.4 minutes with m/z 1552.6 [M+H]$^+$ consistent with the expected product mass.

$^1$H NMR, 500 MHz (DMSO, 25° C.): 8.45-7.50 ppm (m, 6H), 5.15-4.25 ppm (m, 9.8H), 4.2-3.35 ppm (m, 25H), 3.25-3.05 ppm (m, 1H).

Example 11

5,5'-(2,4-dihydroxypentane-1,5-diyl)bis(formylazanediyl)bis($N^1,N^3$-bis(1,3-dihydroxypropan-2-yl)-2,4,6-triiodoisophthalamide)

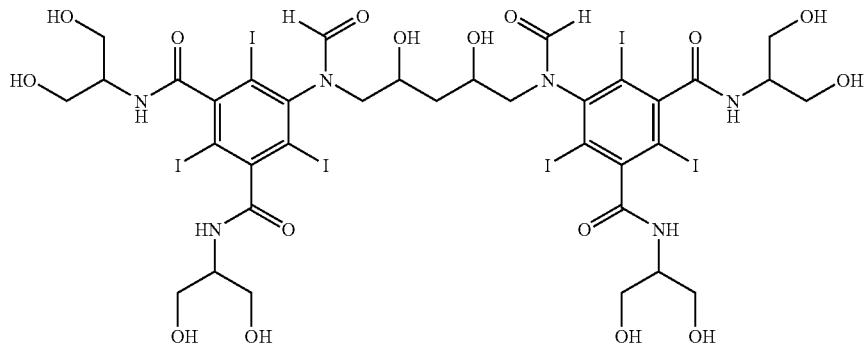 [SMILES: O=CN(CC(O)CC(O)CN(C=O)c1c(I)c(C(=O)NC(CO)CO)c(I)c(C(=O)NC(CO)CO)c1I)c1c(I)c(C(=O)NC(CO)CO)c(I)c(C(=O)NC(CO)CO)c1I]

To a stirred slurry of 1-formamido-3,5-bis(1,3-bis(formyloxy)propan-2-ylcarbamoyl)-2,4,6-triiodo-benzene (Example 9a) (11.5 g, 13.6 mmol) in water (5 ml) and methanol (5 ml) was added solid boric acid (0.60 g, 9.6 mmol). A potassium hydroxide solution (10 M)) was then added drop wise to maintain the pH at pH 12.6. To the clear solution was added 1,4-pentadiene diepoxide (0.48 g, 4.8 mmol). The pH was maintained between pH 12.6-13 by addition of solid boric acid. The reaction was left over night and a new portion of 1,4-pentadiene diepoxide (0.20 g, 2.0 mmol) was added and the reaction left for two days. The reaction mixture was neutralized by addition of hydrochloric acid (18%) and treated with ion exchangers (AMB200C, 36 ml) and (IRA67, 36 ml). The resins were filtered off and rinsed with water and the combined aqueous solution was reduced in vacuo. The crude product was purified by preparative HPLC (column Phenomenex Luna C18 10 μm 250×50.0 mm, solvents: A=water and B=acetonitrile; gradient 05-15% B over 60 min; flow 50.0 ml/min) After freeze drying 2.52 g 5,5'-(2,4-dihydroxypentane-1,5-diyl)bis(formylazanediyl)bis($N^1,N^3$-bis(1,3-dihydroxypropan-2-yl)-2,4,6-triiodoisophthalamide) was obtained (24% yield).

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave four peaks centred at 9.4 minutes with m/z 1566.7 [M+H]$^+$ consistent with the expected product mass.

$^1$H NMR, 500 MHz (DMSO, 25° C.): 8.25-7.50 ppm (m, 6H), 5.25-4.25 ppm (m, 10H), 4.25-3.35 ppm (m, 24.5H), 3.30-2.80 ppm (m, 1.6H), 1.90-13.5 ppm (m, 2H).

Example 12

5,5'-(2,3-dihydroxybutane-1,4-diyl)bis(formylazanediyl)bis(N[1]-(2,3-dihydroxypropyl)-N[3]-(2-hydroxyethyl)-2,4,6-triiodoisophthalamide)

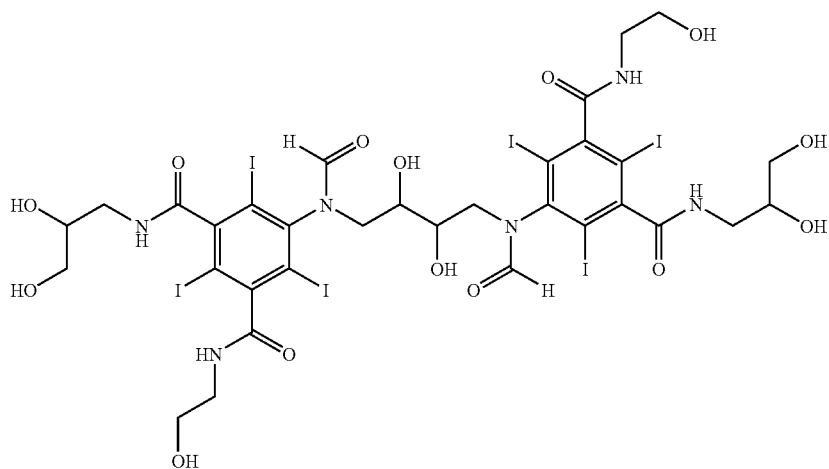 [SMILES: O=CN(CC(O)C(O)CN(C=O)c1c(I)c(C(=O)NCCO)c(I)c(C(=O)NCC(O)CO)c1I)c1c(I)c(C(=O)NCCO)c(I)c(C(=O)NCC(O)CO)c1I]

To a stirred suspension of 3-(3-formamido-5-(2-(formyloxy)ethylcarbamoyl)-2,4,6-triiodobenzamido)propane-1,2-diyl diformate (Example 13a) (92.0 g, 116.9 mmol) in water (117 ml) and methanol (117 ml) was added solid boric acid (14.5 g, 233.8 mmol). A potassium hydroxide solution (10 M) was then added drop wise to maintain the pH at pH 11.5. 1,3-Butadiene diepoxide (3.5 g, 40.9 mmol) was added drop wise. The pH was maintained at 11.6 by continuous addition of potassium hydroxide (10 M) for several hours. The reaction was left stirring over night and then neutralized by addition of hydrochloric acid (18% w) and treated with ion exchangers (AMB200C, 900 ml) and (IRA67, 900 ml). The resins were filtered off and rinsed with water and the combined aqueous solution was reduced in vacuo. The crude product was purified by preparative HPLC (column Luna C18 10 μm 250×75 mm, solvents: A=water and B=acetonitrile; gradient 02-10% B over 30 min; flow 175 ml/min, UV detection at 214 nm and 254 nm). After freeze drying 36.65 g 5,5'-(2,3-dihydroxybutane-1,4-diyl)bis(formylazanediyl)bis(N[1]-(2,3-dihydroxypropyl)-N[3]-(2-hydroxyethyl)-2,4,6-triiodoisophthalamide) (60% yield) was obtained.

LC-MS (column Luna C18 3 μm 2.0×20 mm, solvents: A=water/0.1% triflouroacetic acid and B=acetonitrile/0.1% trifluoroacetic acid; gradient 0-20% B over 5 min; flow 0.6 ml/min, UV detection at 214 and 254 nm, ESI-MS) gave a multiple peak centred at 2.5 minutes with m/z 1492.7 [M+H]+ consisten with the wanted structure.

$^1$H-NMR 500 MHz (solvent: $D_2O$, ref. $H_2O$=4.8 ppm, 25° C.): 8.47 ppm (m, 1H), 8.24 ppm (m, 1H), 4.40-3.35 ppm (m, 24H).

Example 13

5,5'-(2-hydroxypropane-1,3-diyl)bis(formylazanediyl)bis(N[1]-(2,3-dihydroxypropyl)-N[3]-(2-hydroxyethyl)-2,4,6-triiodoisophthalamide)

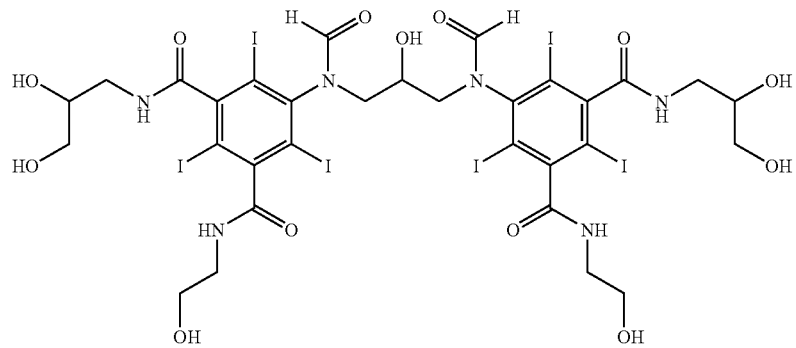 [SMILES: O=CN(CC(O)CN(C=O)c1c(I)c(C(=O)NCCO)c(I)c(C(=O)NCC(O)CO)c1I)c1c(I)c(C(=O)NCCO)c(I)c(C(=O)NCC(O)CO)c1I]

13a) 3-(3-formamido-5-(2-(formyloxy)ethylcarbamoyl)-2,4,6-triiodobenzamido)propane-1,2-diyldiformate Formic acid (400 ml) was charged in a dry 2000 ml flask fitted with dropping funnel, stir bar, thermometer and gas inlet. The acid was cooled on ice bath under a nitrogen blanket and acetic anhydride (218 ml, 1.986 mol) was added drop wise over 2 h over 2 h not allowing the temperature to exceed 4.5° C. After complete addition the temperature was allowed to reach 10° C. and the ice bath was put back. When the mixture was cooled to 3° C., 5-amino-N-(2,3-dihydroxypropyl)-N'-(2-hydroxyethyl)-2,4,6-triiodo-isopthalamide (140 g, 198.6 mmol) was added and the mixture was left stirring over night. The now homogenous solution was evaporated to dryness in vacuo at 40° C. and used without purification in the next step.

The obtained product does contain some minor fraction of O-acetyl esters, as the product is used directly in the next step without purification this can be disregarded.

13b) 5,5'-(2-hydroxypropane-1,3-diyl)bis(formylazanediyl)bis($N^1$-(2,3-dihydroxypropyl)-$N^3$-(2-hydroxyethyl)-2,4,6-triiodoisophthalamide)

To a stirred suspension of 3-(3-formamido-5-(2-(formyloxy)ethylcarbamoyl)-2,4,6-triiodobenzamido)propane-1,2-diyldiformate (3.0 g, 3.9 mmol) in water (3 ml) and methanol (3 ml) was added solid boric acid (0.48 g, 7.8 mmol). A potassium hydroxide solution (10 M) was then added drop wise to maintain the pH at pH 11.5. Epichlorohydrin (130 mg, 1.4mmol) was added. The pH was maintained at 11.6 by continuous addition of potassium hydroxide (10 M) for several hours. The reaction was left stirring over night and then neutralized by addition of hydrochloric acid (18% w) and treated with ion exchangers (AMB200C, 30 ml) and (IRA67, 30 ml). The resins were filtered off and rinsed with water and the combined aqueous solution was reduced in vacuo.

The crude product was purified by preparative HPLC (column Luna C18 10 μm 250×50 mm, solvents: A=water and B=acetonitrile; gradient 05-12% B over 30 min; flow 70.0 ml/min, UV detection at 214 nm and 254 nm). After freeze drying 1.03 g 5,5'-(2-hydroxypropane-1,3-diyl)bis(formylazanediyl)bis($N^1$-(2,3-dihydroxypropyl)-$N^3$-(2-hydroxyethyl)-2,4,6-triiodoisophthalamide) (50%) was obtained.

LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a multitude of isomeric peaks between 9.5 and 11 minutes with m/z 1462.6 [M+H]$^+$ corresponding to the wanted structure.

$^1$H-NMR 500 MHz (solvent: D$_2$O, ref. H$_2$O=4.8 ppm, 25° C.): 8.35 ppm (m, 1.1H), 8.10 ppm (m, 0.85H), 4.20-3.25 ppm (m, 23H).

Example 14

5,5'-(2,4-dihydroxypentane-1,5-diyl)bis(formylazanediyl)bis($N^1$-(2,3-dihydroxypropyl)-$N^3$-(2-hydroxyethyl)-2,4,6-triiodoisophthalamide)

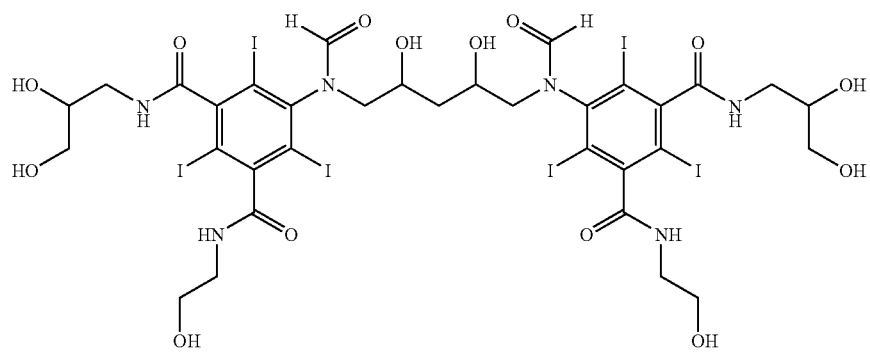 [SMILES: O=CN(CC(O)CC(O)CN(C=O)c1c(I)c(C(=O)NCCO)c(I)c(C(=O)NCC(O)CO)c1I)c1c(I)c(C(=O)NCCO)c(I)c(C(=O)NCC(O)CO)c1I]

To a stirred suspension of 3-(3-formamido-5-(2-(formyloxy)ethylcarbamoyl)-2,4,6-triiodobenzamido)propane-1,2-diyldiformate (Example 13a) (3.1 g, 4.0 mmol) in water (3 ml) and methanol (3 ml) was added solid boric acid (0.49 g, 8.0 mmol). A potassium hydroxide solution (10 M) was then added drop wise to maintain the pH at pH 11.5. 1,4-Pentadiene diepoxide (0.14 g, 1.40 mmol) was added. The pH was maintained at 11.6 by continuous addition of potassium hydroxide (10 M) for several hours. The reaction was left over night. A new portion 1,4-pentadiene diepoxide (0.12 g, 1.2 mmol) was added and the reaction left for two days. The reaction mixture was neutralized by addition of hydrochloric acid (18% w) and treated with ion exchangers (AMB200C, 30 ml) and (IRA67, 30 ml). The resins were filtered off and rinsed with water and the combined aqueous solution was reduced in vacuo. The crude product was purified by preparative HPLC (column Luna C18 10 μm 250×50 mm, solvents: A=water and B=acetonitrile; gradient 5-12% B over 30 min; flow 70.0 ml/min, UV detection at 214 nm and 254 nm). After freeze drying 352 mg 5,5'-(2,4-dihydroxypentane-1,5-diyl)bis(formylazanediyl)bis($N^1$-(2,3-dihydroxypropyl)-$N^3$-(2-hydroxyethyl)-2,4,6-triiodoisophthalamide) (12% yield) was obtained.

LC-MS (column Luna C18 3 μm 2.0×20 mm, solvents: A=water/0.1% triflouroacetic acid and B=acetonitrile/0.1% trifluoroacetic acid; gradient 0-20% B over 5 min; flow 0.6 ml/min, UV detection at 214 and 254 nm, ESI-MS) gave a multiple peak centred at 2.8 minutes with m/z 1506.8 [M+H]$^+$ corresponding to the wanted structure.

¹H-NMR 500 MHz (solvent: D₂O, ref. H₂O=4.8 ppm, 25° C.): 8.35 ppm (m, 1H), 8.10 ppm (m, 1H), 4.30-2.85 ppm (m, 24H), 1.80-1.40 ppm (m, 2H).

Example 15

5,5'-(2-hydroxypropane-1,3-diyl)bis(formylazanediyl)bis(N¹-(1,3-dihydroxypropan-2-yl)-N³-(2,3-dihydroxypropyl)-2,4,6-triiodoisophthalamide)

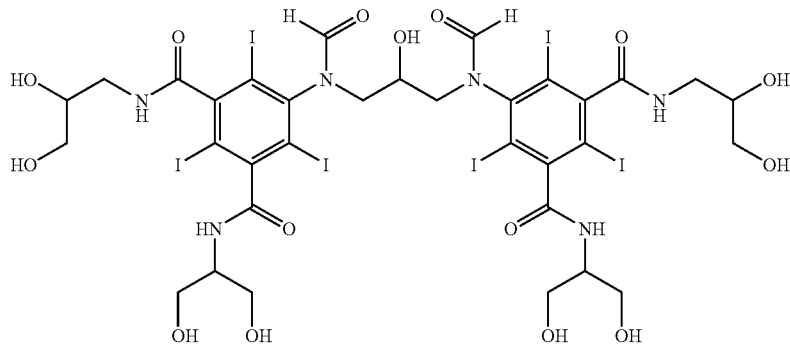 [SMILES: O=CN(CC(O)CN(C=O)c1c(I)c(C(=O)NCC(O)CO)c(I)c(C(=O)NC(CO)CO)c1I)c1c(I)c(C(=O)NCC(O)CO)c(I)c(C(=O)NC(CO)CO)c1I]

15a) 5-amino-N¹-(1,3-dihydroxypropan-2-yl)-N³-(2,3-dihydroxypropyl)-2,4,6-triiodoisophthalamide At 2° C. a mantled reactor with mechanical stirrer, dropping funnel and inner thermometer was charged with DMA (640 ml), triethylamine (224 ml, 161.3 g, 1.59 mol) and 5-Amino-2,4,6-triiodo-isophthalic acid dichloride (320 g, 537 mmol). The mixture was stirred and cooled to −24° C. A solution of 1-amino-2,3-dihydroxypropane (49,92 g, 548 mmol) in DMA (160 ml) was added slowly to keep the inner temperature below −19° C. The mixture was stirred at a temperature gradient from −24° C. to 0° C. in 24 h. A solution of serinol (60 g, 658 mmol) in DMA (160 ml) was added slowly and the mixture was stirred at a temperature gradient from 0° C. to 40° C. in 20 h. The mixture was stirred at 22° C. for 1 day and precipitated triethylamine hydrochloride was filtered off. Evaporation at 60° C./25 mbar left a viscous liquid residue (586 g) which was diluted with water (350 ml). Salts and excess amines were removed by treatment with ion exchangers Amberlite200C (143 ml), IRA67 (148 ml) and IRA900 (56 ml) followed by filtration. The ion exchangers were washed with water (2×400 ml). Some seeding crystals were added to the combined aqueous phase and the solution was stirred slowly at 22° C. for 9 days. The precipitate was isolated by filtration. The filter cake was re-suspended in water (240 ml) and stirred for 1 day. The suspension was filtered and the filter cake was dried in air (216 g, 57% yield, 88.6% HPLC purity). The crude product was purified by preparative HPLC (column: selfpacked Luna C18, 10 μm 250×100 mm, solvents: A=water and B=acetonitrile; gradient 5-10% B over 10 min, hold 10 min; flow 350 ml/min, UV detection at 244 nm and 254 nm). Relevant fractions were combined and freeze dried to yield 5-amino-N¹-(1,3-dihydroxypropan-2-yl)-N³-(2,3-dihydroxypropyl)-2,4,6-triiodoisophthalamide.

LC-ESI-MS) m/z 705.9 [M+H]⁺ corresponding to the wanted structure.

¹H-NMR 500 MHz (solvent: DMSO-d6, ref. TMS): side chain 1: 8.34 ppm (m, NH), 7.91 ppm (m, NH), 4.8-4.4 ppm (m, OH), 3.70 ppm (m, CH), 3.49 ppm (m, CH2), 3.39 ppm (m, CH2), 3.31 ppm (m, NCH2), 3.14 ppm (m, NCH2), side chain 2: 8.09 ppm (d, NH), 7.58 ppm (m, NH), 4.8-4.4 ppm (m, OH), 3.82 ppm (m, CH), 3.65 ppm (m, CH2), 3.53 ppm (m, CH2), side chain 3: 5.46 ppm (m, NH2).

15b) 3-(3-(1,3-bis(formyloxy)propan-2-ylcarbamoyl)-5-formamido-2,4,6-triiodobenzamido)propane-1,2-diyldiformate This compound was made in a manner analogous to the preparation described in example 1a.

¹H-NMR 500 MHz (solvent: DMSO-d6, ref TMS): 10.30-10.16 ppm and 10.00-9.93 ppm (m, 1H, NHCHO), δ 8.34-8.30 ppm and 7.94-7.82 ppm (m, 1H, NHCHO), δ 9.13-8.46 ppm (m, 2H, ArCONH), δ 8.31-8.21 ppm (m, 4H, OCHO), δ 5.31-5.04 ppm (m, 1H, APD CHO-CHO), δ 4.54-3.89 ppm (m, 7H, APD & serinol CH2O—CHO and serinol ArNHCH), δ 3.08-3.72 ppm (m, 2H, APD ArNHCH2).

15c) 5,5'-(2-hydroxypropane-1,3-diyl)bis(formylazanediyl)bis(N¹-(1,3-dihydroxypropan-2-yl)-N³-(2,3-dihydroxypropyl)-2,4,6-triiodoisophthalamide)

A 250 ml mantled reactor fitted with thermometer, stir bar, dropping funnel and pH-electrode was cooled by a cryostat to 10 C. Into the reactor was charged methanol (17.6 ml), water (19.6 ml) and boric acid (2.33 g, 373 mmol) followed by aqueous potassium hydroxide (10 M, 50.4 ml) to dissolve the boric acid. The starting material, 3-(3-(1,3-bis(formyloxy)propan-2-ylcarbamoyl)-5-formamido-2,4,6-triiodobenzamido)propane-1,2-diyldiformate (16.8 g, 19.9 mmol) was added and a drop wise addition of potassium hydroxide was started to maintain the pH within 10.7-11.2 while keeping the temperature between 10-14° C. After 40 min epichlorohydrin (0.89 g, 9.62 mmol) was added while maintaining the pH at 11.6-11.7 with occasional addition of either potassium hydroxide (10 M) or solid boric acid. The temperature was maintained at 10° C. for the remainder of the experiment. The mixture was stirred for 5 h and the pH was adjusted to 11.7 and left stirring for 48 while maintaining the pH between 11.6-11.7. The reaction mixture was quenched by addition of hydrochloric acid (6 M, 6.0 ml) to attain a pH of 7.5. Water (200 ml) was added followed by acidic ion exchanger AMB200C (94 ml, 158 meq) and the mixture was stirred for 1 h. Basic ion exchanger IRA67 (150 ml, 158 meq) was added and the mixture was stirred for 1 h. The ion exchangers were filtered off and rinsed with water (600 ml) in portions. The combined filtrate was reduced in vacuo and the crude product was purified by preparative HPLC (column: Phenomenex Luna C18, 10 μm 248×101 mm, solvents: A=water and B=acetonitrile; gradient 5-20% B over 35 min; flow 300 ml/min, UV detection at 214 nm and 254 nm). After freeze drying 7.3 g 5,5'-(2-hydroxypropane-1,3-diyl)bis(formylazanediyl)bis(N¹-(1,3-dihydroxypropan-2-yl)-N³-(2,3-dihydroxypropyl)-2,4,6-triiodoisophthalamide) (49.0% yield) was obtained.

LC-ESI-MS) m/z 1522.5 [M+H]$^+$ and its sodium adduct corresponding to the wanted structure.

$^1$H-NMR 500 MHz (solvent: D$_2$O, ref. H$_2$O=4.8 ppm, 25° C.): 8.5 ppm, 8.2 ppm (m, 2H, HCO); 4.7 ppm-3.0 ppm (m, 25H, CH, CH2), side chain 1: 4.06 ppm (m, CH); 3.80 ppm, 3.68 ppm (m, CH2OH); 3.59 ppm, 3.47 ppm (m, NCH2), side chain 2: 4.18 ppm (m, CH), 3.87 ppm (m, CH2), bridge: 8.48 ppm, 8.26 ppm (m, 2H, HCO)

Example 16

5,5'-(2,3-dihydroxybutane-1,4-diyl)bis(formylazanediyl)bis(N$^1$-(1,3-dihydroxypropan-2-yl)-N$^3$-(2,3-dihydroxypropyl)-2,4,6-triiodoisophthalamide)

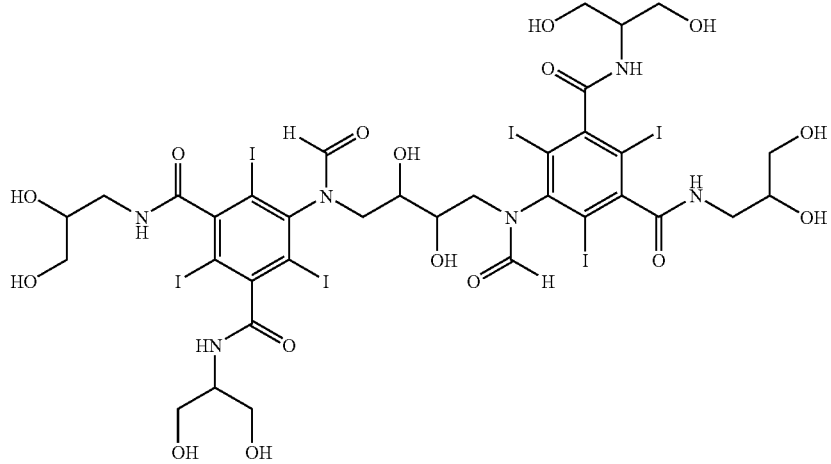 [SMILES: O=CN(CC(O)C(O)CN(C=O)c1c(I)c(C(=O)NCC(O)CO)c(I)c(C(=O)NC(CO)CO)c1I)c1c(I)c(C(=O)NCC(O)CO)c(I)c(C(=O)NC(CO)CO)c1I]

A 250 ml mantled reactor fitted with thermometer, stir bar, dropping funnel and pH-electrode was cooled by a cryostat to 10° C. Into the reactor was charged methanol (15.1 ml), water (22.1 ml) and boric acid (2.33 g, 373 mmol) followed by aqueous potassium hydroxide (10 M, 50.4 ml) to dissolve the boric acid. The starting material, 3-(3-(1,3-bis(formyloxy)propan-2-ylcarbamoyl)-5-formamido-2,4,6-triiodobenzamido)propane-1,2-diyldiformate (Example 15b)(16.8 g, 19.9 mmol) was added and a drop wise addition of potassium hydroxide was started to maintain the pH within 10.7-11.7 while keeping the temperature between 10-14° C. After 40 min butadiene-1,3-diepoxide (0.826 g, 9.59 mmol) was added while maintaining the pH at 11.6-11.7 with occasional addition of either potassium hydroxide (10 M) or solid boric acid. The temperature was maintained at 10° C. for the remainder of the experiment. The mixture was stirred for 7 h and the pH was adjusted to 11.35 and left stirring over the night.

The following day the reaction mixture was quenched by addition of hydrochloric acid (6 M, 6.0 ml) to attain a pH of 7.5. Water (200 ml) was added followed by acidic ion exchanger AMB200C (94 ml, 158 mq) and the mixture was stirred for 1 h. Basic ion exchanger IRA67 (150 ml, 158 mq) was added and the mixture was stirred for 1 h. The ion exchangers were filtered off and rinsed with water (600 ml) in portions. The combined filtrate was reduced in vacuo and the crude product was purified by preparative HPLC (column: Phenomenex Luna C18, 10 μm 248×101 mm, solvents: A=water and B=acetonitrile; gradient 5-15% B over 35 min; flow 300 ml/min, UV detection at 214 nm and 254 nm). After freeze drying 3.12 g 5,5'(2,3-dihydroxybutane-1,4-diyl)bis(formylazanediyl)bis(N$^1$-(1,3-dihydroxypropan-2-yl)-N$^3$-(2,3-dihydroxypropyl)-2,4,6-triiodoisophthalamide) (21.4% yield) was obtained.

LC-ESI-MS) m/z:1552.5 [M+H]$^+$ and its sodium adduct corresponding to the wanted structure.

$^1$H-NMR 500 MHz (solvent: D$_2$O, ref. H$_2$O=4.8 ppm, 25° C.): 8.5 ppm, 8.2 ppm (m, 2H, HCO); 4.4 ppm-3.0 ppm (m, 26H, CH, CH2), side chain 1: 4.06 ppm (m, CH); 3.80 ppm, 3.68 ppm (m, CH2OH); 3.59 ppm, 3.47 ppm (m, NCH2), side chain 2: 4.18 ppm (m, CH), 3.87 ppm (m, CH2), bridge: 8.48 ppm, 8.26 ppm (m, 2H, HCO)

Example 17

5,5'-(2,4-dihydroxypentane-1,5-diyl)bis(formylazanediyl)bis(N$^1$-(1,3-dihydroxypropan-2-yl)-N$^3$-(2,3-dihydroxypropyl)-2,4,6-triiodoisophthalamide)

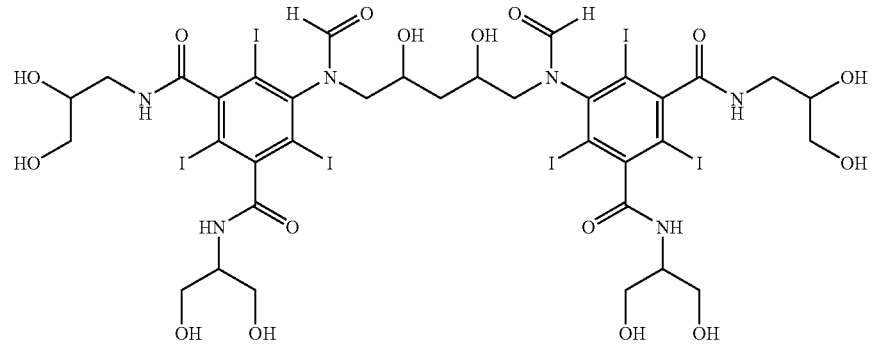 [SMILES: O=CN(CC(O)CC(O)CN(C=O)c1c(I)c(C(=O)NCC(O)CO)c(I)c(C(=O)NC(CO)CO)c1I)c1c(I)c(C(=O)NCC(O)CO)c(I)c(C(=O)NC(CO)CO)c1I]

A 250 ml mantled reactor fitted with thermometer, stir bar, dropping funnel and pH-electrode was cooled by a cryostat to 10° C. Into the reactor was charged methanol (12.6 ml), water (24.6 ml) and boric acid (2.33 g, 373 mmol) followed by aqueous potassium hydroxide (10 M, 50.4 ml) to dissolve the boric acid. The starting material, 3-(3-(1,3-bis(formyloxy)propan-2-ylcarbamoyl)-5-formamido-2,4,6-triiodobenzamido)propane-1,2-diyl diformate (Example 15b)(16.8 g, 19.9 mmol) was added and a drop wise addition of potassium hydroxide was started to maintain the pH within 10.7-11.2 while keeping the temperature between 10-14° C. After 15 min pentadiene-1,4-diepoxide (0.99 g, 9.89 mmol) was added while maintaining the pH at 11.5-11.6 with occasional addition of either potassium hydroxide (10 M) or solid boric acid. Under stirring for 30 h, the temperature was maintained at 10° C. and the pH was maintained between 11.5-11.6. The temperature was now adjusted to 23° C. and the mixture was left stirring over the night. The following day a second portion of pentadienediepoxide (0.63 g, 6.27 mmol) was added and the mixture was stirred for three days. The reaction mixture was quenched by addition of hydrochloric acid (6 M, 6.0 ml) to attain a pH of 7.5. Water (200 ml), acidic ion exchanger AMB200C (94 ml, 158 meq) and basic ion exchanger IRA67 (150 ml, 158 mq) was added and the mixture was stirred for 1 h. The ion exchangers were filtered off and rinsed with water (600 ml) in portions. The combined filtrate was reduced in vacuo and purified by preparative HPLC.

The combined filtrate was reduced in vacuo and the crude product was purified by preparative HPLC (column: Phenomenex Luna C18, 10 μm 248×101 mm, solvents: A=water and B=acetonitrile; gradient 5-15% B over 35 min; flow 300 ml/min, UV detection at 214 nm and 254 nm). After freeze drying 6.6 g 5,5'-(2,4-dihydroxypentane-1,5-diyl)bis(formylazanediyl)bis(N$^1$-(1,3-dihydroxypropan-2-yl)-N$^3$-(2,3-dihydroxypropyl)-2,4,6-triiodoisophthalamide) (42.5% yield) was obtained.

LC-ESI-MS) m/z:1566.4 [M+H]$^+$ and its sodium adduct corresponding to the wanted structure.

$^1$H-NMR (solvent: D2O, ref. H2O=4.8 ppm): 8.5 ppm, 8.2 ppm (m, 2H, HCO); 4.4 ppm-3.0 ppm (m, 26H, CH, CH2); 2.0 ppm-1.6 ppm (m, 2H, CH2), side chain 1: 4.06 ppm (m, 2H, CH); 3.80 ppm, 3.68 ppm (m, 4H, CH2OH); 3.59 ppm, 3.47 ppm (m, 4H, NCH2), side chain 2: 4.18 ppm (m, 2H, CH), 3.87 ppm (m, 8H, CH2), bridge: 8.48 ppm, 8.26 ppm (m, 2H, HCO); 1.97 ppm-1.62 ppm (m, 2H, CH2)

Example 18

5,5'-(2-hydroxypropane-1,3-diyl)bis(formylazanediyl)bis(N$^1$-(1,3-dihydroxypropan-2-yl)-N$^3$-(2-hydroxyethyl)-2,4,6-triiodoisophthalamide)

18a) 5-amino-N$^1$-(1,3-dihydroxypropan-2-yl)-N$^3$-(2-hydroxyethyl)-2,4,6-triiodoisophthalamide 2-Amino-1,3-propanediol (15.66 g, 171.89 mmol) was placed in a 2 l, one-necked round-bottomed flask and N,N'-dimethylacetamide (520 ml) was added. Stirring was started and a clear and colorless solution was obtained to which was added triethylamine (85.8 ml, 619.2 mmol). 5-amino-2,4,6-triiodoisophthaloyl dichloride (102.4 g, 191 89 mmol) was added in portions. The mixture was left stirring at ambient temperature for 25 hours and ethanolamine (10.34 ml, 171.89 mmol) was added. Stirring was continued at ambient temperature for 3 days.

Precipitated Et$_3$N HCl salt was filtered off and washed with N,N'-dimethylacetamide (30 ml). The combined organic phases were evaporated to a thick oil in vacuo, to the oil was added ethanol (400 ml) and the mixture was vigorously stirred at ambient temperature for three days. The formed precipitate was collected by filtration and washed with ethanol (50 ml) and dried in vacuo.

The crude product was slightly brown color solid. Yield: 98.15 g.

HPLC showed the wanted compound to be present in 78% chemical yield.

The product was used in the next step without further purification.

LC-MS:(ESI Ion-Trap, m/e): 675.8 [M+H]$^+$.

$^1$H-NMR 500 MHz (solvent: D$_2$O, ref. H$_2$O=4.8 ppm, 25° C.): Side chain 1: 8.38 ppm (m, NH), 8.05 ppm (m, NH), 4.7-4.4 ppm (m, OH), 3.25 ppm (m, CH2N), 3.52 ppm (m, CH2), side chain 2: 8.09 ppm (d, NH), 7.56 ppm (m, NH), 4.7-4.4 ppm (m, OH), 3.81 ppm (m, CH), 3.65 ppm (m, CH2), 3.55 ppm (m, CH2), side chain 3: 5.43 ppm (m, NH2)

18b) 2-(3-(2-acetoxyethylcarbamoyl)-5-amino-2,4,6-triiodobenzamido)propane-1,3-diyl diacetate Acetic anhydride (312 ml, 3.3 mmol) was added drop wise to an ice cooled solution of the crude product obtained in example 18a (100 g, 0.15 mmol) in pyridine (600 ml) over 30 minutes. The cooling bath was then removed and stirring was continued overnight. Ethanol (200 ml) was added to the mixture under ice cooling and the mixture was reduced in vacuo, ethyl acetate (400 ml) was added to dark coloured oil. The solution was placed in a refrigerator overnight to complete crystallisation. The product was collected by filtration and washed with ethyl acetate, 1N HCl (1×200 ml), water (2×200 ml) and oven dried (50° C.).

The crude product was purified by preparative HPLC (column Phenomenex, Luna C18 10 μm, 248×101 mm, solvents:

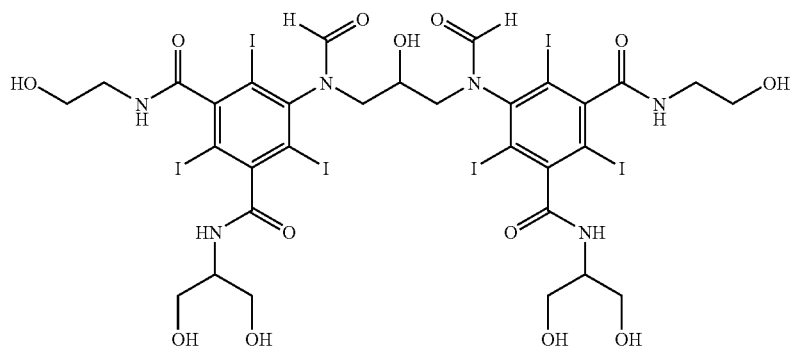 [SMILES: O=CN(CC(O)CN(C=O)c1c(I)c(C(=O)NCCO)c(I)c(C(=O)NC(CO)CO)c1I)c1c(I)c(C(=O)NCCO)c(I)c(C(=O)NC(CO)CO)c1I]

A=water and B=acetonitrile; gradient 25-27% B in 6 min, continued for 30 min; flow 300 ml/min, UV detection at 214 nm and 254 nm). Pooled fractions were reduced in vacuo whereupon the product could be recovered by filtration. The product was dried at 60° C. in vacuo to yield 73 g 2-(3-(2-acetoxyethylcarbamoyl)-5-amino-2,4,6-triiodobenzamido) propane-1,3-diyldiacetate (60.8% yield).

LC-MS: (ESI Ion-Trap, m/e): 801.6 [M+H]$^+$ $^1$H NMR, 500 MHz (DMSO-d6, 25° C.): 2.0 ppm (m, 9H), 3.2 ppm (triplet, 2H), 4.10 ppm (m, 6H), 4.19 ppm (m, 1H), 5.25 ppm (m, NH2), 8.15 ppm (m, NH), 8.27 ppm (m, NH), 8.3 ppm (m, NH), 8.38 ppm (m, NH).

18c) $N^1$-(1,3-dihydroxypropan-2-yl)-5-formamido-$N^3$-(2-hydroxyethyl)-2,4,6-triiodoisophthalamide Acetic anhydride (19.47 ml, 20.6 mmol) was added to formic acid (100 ml) under ice cooling keeping the temperature below 5° C. After complete addition the cooling-bath was removed and the temperature was allowed to reach 10° C. The ice cooling was continued and 2-(3-(2-acetoxyethylcarbamoyl)-5-amino-2,4,6-triiodobenzamido)propane-1,3-diyldiacetate (33 g, 41.2 mmol) was then added in portions over 3 minutes. The mixture was left to stir overnight and then evaporated in vacuo to afford a white foam to which methanol (100 ml) and water (100 ml) was added. While stirring, 10N NaOH was added drop wise until a clear solution was obtained. Drop wise addition of 10N NaOH was continued until pH stabilized at 11.60. Methanol was removed from the mixture by evaporation in vacuo and the solution was acidified to pH 2.7 with 18.6% HCl. The mixture was placed in a refrigerator overnight and the product, precipitated from the solution was collected, washed with water and dried at 60° C. to afford 24 g of $N^1$-(1,3-dihydroxypropan-2-yl)-5-formamido-$N^3$-(2-hydroxyethyl)-2,4,6-triiodoisophthalamide (82.9% yield).

was dissolved in a solution of potassium hydroxide (1.01 g, 17.9 mmol) in methanol (8 ml) and water (8 ml). The temperature was raised to 40 C and boric acid (0.62 g, 1.91 mmol) was added. Heating was continued at this temperature for 15 minutes. After cooling to ambient temperature, stirring was continued for 4 hours before epichlorohydrin (0.37 g, 3.98 mmol) was added. pH was maintained between 12-13 for 5 hours by addition of boric acid. The next day, pH was adjusted to 3.97 and methanol was removed in vacuo. The remaining aqueous solution was diluted with water (75 ml) and treated with ion exchangers (AMB 200C, H$^+$ and IRA-67, OH$^-$) to zero conductivity. The ion exchangers were filtered off and rinsed with water and the combined filtrates were freeze-dried. And purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying 3.80 g 5,5'-(2-hydroxypropane-1,3-diyl)bis(formylazanediyl)bis($N^1$-(1,3-dihydroxypropan-2-yl)-$N^3$-(2-hydroxyethyl)-2,4,6-triiodoisophthalamide) was obtained (66% yield).

LC-MS: (ESI Ion-Trap, m/e): 1462.7 [M+H]$^+$ $^1$H-NMR 500 MHz (solvent: D$_2$O, ref. H$_2$O=4.8 ppm, 25° C.): side chain 1: 3.58 ppm (m, NCH2), 3.87 ppm (m, CH2OH), side chain 2: 4.19 ppm (m, 2H, CH), 3.87 ppm (m, CH2), bridge: 8.47 ppm, 8.20 ppm (m, 2H, NHCO)

Example 19

5,5'-(2,3-dihydroxybutane-1,4-diyl)bis(formylazanediyl)bis($N^1$-(1,3-dihydroxypropan-2-yl)-$N^3$-(2-hydroxyethyl)-2,4,6-triiodoisophthalamide)

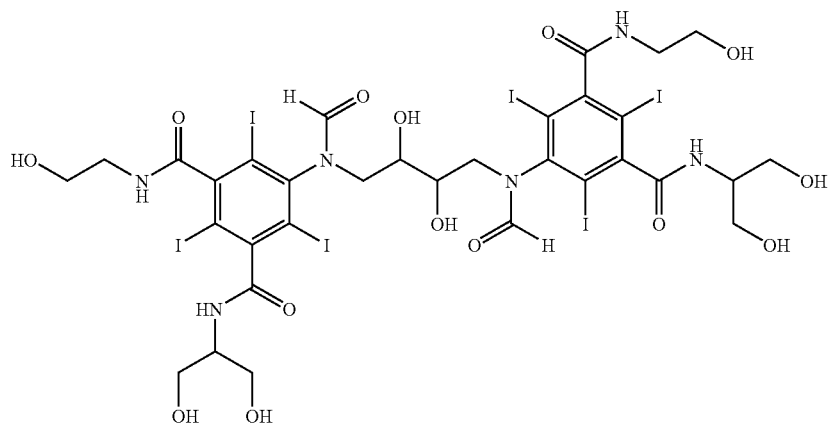 [SMILES: O=CN(CC(O)C(O)CN(C=O)c1c(I)c(C(=O)NCCO)c(I)c(C(=O)NC(CO)CO)c1I)c1c(I)c(C(=O)NCCO)c(I)c(C(=O)NC(CO)CO)c1I]

LC-MS: (ESI Ion-Trap), m/e: 703.8 [M+H]$^+$ $^1$H-NMR 500 MHz (solvent: D$_2$O, ref. H$_2$O=4.8 ppm, 25° C.): Side chain 1: 3.59 ppm (m, 2H, CH2N), 3.87 ppm (m, 2H, CH2OH), side chain 2: 4.20 ppm (m, 1H, CH), 3.59 ppm (m, 4H, CH2), side chain 3 : 8.47 ppm (m, 1H, HCO)

18d) 5,5'-(2-hydroxypropane-1,3-diyl)bis(formylazanediyl)bis($N^1$-(1,3-dihydroxypropan-2-yl)-$N^3$-(2-hydroxyethyl)-2,4,6-triiodoisophthalamide)

$N^1$-(1,3-dihydroxypropan-2-yl)-5-formamido-$N^3$-(2-hydroxyethyl)-2,4,6-triiodoisophthalamide (8 g, 11.4 mmol)

Potassium hydroxide (10 M) was added drop wise to a stirring suspension of $N^1$-(1,3-dihydroxypropan-2-yl)-5-formamido-$N^3$-(2-hydroxyethyl)-2,4,6-triiodoisophthalamide (Example 18c) (6 g, 8.5 mmol) in water (5 ml) and methanol (5 ml. The pH was continuously monitored and when pH 11.6 was reached, boric acid (0.46 g, 7.5 mmol) followed by 1,3-butadiene diepoxide (234 μl, 2.99 mmol). The pH of the solution was continuously maintained at the interval 11.5-11.8 by addition of either solid boric acid or potassium hydroxide (10 M). Gradually a clear and colourless solution resulted after 24 hours at ambient temperature. pH was adjusted to 2.7 with hydrochloric acid (6 M) and methanol was removed in vacuo. The remaining aqueous solution was diluted with water (75 ml) and treated with ion exchangers (AMB 200C, H$^+$ and IRA-67, OH$^-$) to zero conductivity. After freeze drying, the crude was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying 2.04 g of 5,5'-(2,3-dihydroxybutane-1,4-diyl)bis(formylazanediyl)bis(N$^1$-(1,3-dihydroxypropan-2-yl)-N$^3$-(2-hydroxyethyl)-2,4,6-triiodoisophthalamide) was obtained (46% yield).

LC-MS: (ESI Ion-Trap, m/e): 1492.7 [M+H]$^+$ $^1$H-NMR 500 MHz (solvent: D$_2$O, ref. H$_2$O=4.8 ppm, 25° C.): side chain 1 : 3.58 ppm (m, NCH2), 3.87 ppm (m, CH2OH), side chain 2: 4.18 ppm (m, 2H, CH), 3.87 ppm (m, CH2), bridge: 8.48 ppm, 8.26 ppm (m, 2H, NHCO).

Example 20

5,5'-(2,4-dihydroxypentane-1,5-diyl)bis(formylazanediyl)bis(N$^1$-(1,3-dihydroxypropan-2-yl)-N$^3$-(2-hydroxyethyl)-2,4,6-triiodoisophthalamide)

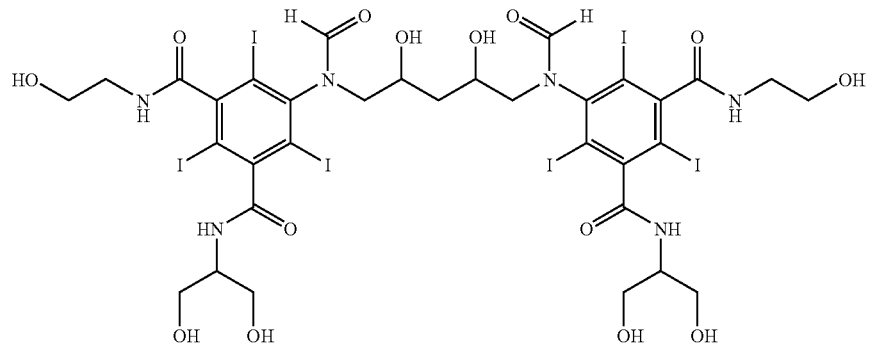 [SMILES: O=CN(CC(O)CC(O)CN(C=O)c1c(I)c(C(=O)NCCO)c(I)c(C(=O)NC(CO)CO)c1I)c1c(I)c(C(=O)NCCO)c(I)c(C(=O)NC(CO)CO)c1I]

Potassium hydroxide (10 M) was added drop wise to a stirring suspension of N$^1$-(1,3-dihydroxypropan-2-yl)-5-formamido-N$^3$-(2-hydroxyethyl)-2,4,6-triiodoisophthalamide (Example 18c) (8.0 g, 11.4 mmol) in water (8 ml) and methanol (8 ml). The pH was continuously monitored and when pH was 11.6, boric acid (0.62 g, 9.9 mmol) was added followed by 1,4-pentadiene diepoxide (400 mg, 3.98 mmol). The pH of the solution was continuously maintained at the interval 11.5-11.8 by addition of either solid boric acid or potassium hydroxide (10 M). Gradually a clear and colourless solution resulted after 24 hours at ambient temperature. pH was adjusted to 3.5 with hydrochloric acid (6 M) and methanol was removed in vacuo. The remaining aqueous solution was diluted with water (75 ml) and treated with ion exchangers (AMB 200C, H$^+$ and IRA-67, OH$^-$) to zero conductivity. After freeze drying the crude was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying 3.16 g of 5,5'-(2,4-dihydroxypentane-1,5-diyl)bis(formylazanediyl)bis(N$^1$-(1,3-dihydroxypropan-2-yl)-N$^3$-(2-hydroxyethyl)-2,4,6-triiodoisophthalamide) was obtained (53% yield)

LC-MS: (ESI Ion-Trap), m/e: 1506.6 [M+H]$^+$.

$^1$H-NMR 500 MHz (solvent: D$_2$O, ref. H$_2$O=4.8 ppm, 25° C.): 8.47 ppm, 8.23 ppm (m, 2H, HCO), 4.40 ppm-3.10 ppm (m, 24 H, CH/CH2), 1.95 ppm-1.60 ppm (m, 2H, CH2).

Example 21

5-(N-(3-(N-(3,5-bis(2,3-dihydroxypropylcarbamoyl)-2,4,6-triiodophenyl)acetamido)-2-hydroxypropyl)formamido)-$N^1$,$N^3$-bis(2,3-dihydroxypropyl)-2,4,6-triiodoisophthalamide

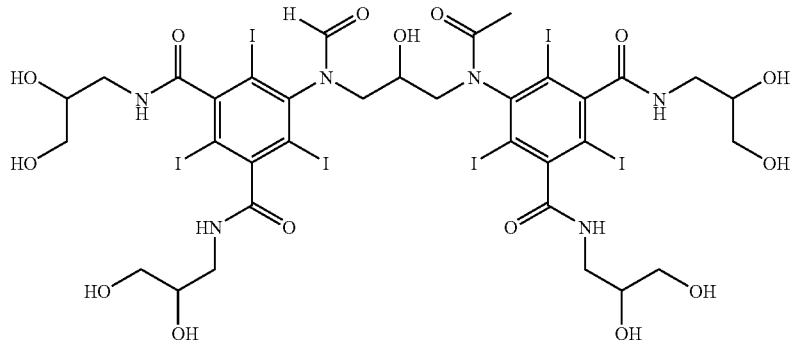 [SMILES: CC(=O)N(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

21a) 5-(N-allylacetamido)-$N^1$,$N^3$-bis(2,3-dihydroxypropyl)-2,4,6-triiodoisophthalamide To a stirred solution of 5-acetamido-$N^1$,$N^3$-bis(2,3-dihydroxypropyl)-2,4,6-triiodoisophthalamide (7.5 g, 10 mmol) and boric acid (1.24 g, 20 mmol) in water (10 ml) and methanol (7 ml) is added potassium hydroxide (10 M) drop wise until a stable pH 12.5 is established. Allylbromide (860 ul, 10 mmol) is added and potassium hydroxide (10 M) is continuously added to maintain pH 12.5. for 3 h and the mixture is then left stirring over night. The following day the mixture is reduced in vacuo to remove methanol, the resulting aqueous phase is diluted with 50 ml water and treated with acidic and basic ion exchanger. Resins are removed and rinsed and the combined aqueous volume is reduced to dryness in vacuo to yield 5-(N-allylacetamido)-$N^1$,$N^3$-bis(2,3-dihydroxypropyl)-2,4,6-triiodoisophthalamide.

21b) 5-(N-(3-(N-(3,5-bis(2,3-dihydroxypropylcarbamoyl)-2,4,6-triiodophenyl)acetamido)-2-hydroxypropyl)formamido)-$N^1$,$N^3$-bis(2,3-dihydroxypropyl)-2,4,6-triiodoisophthalamide To a stirred solution of water (10 ml) and methanol (7 ml) is added 5-(N-allylacetamido)-$N^1$,$N^3$-bis(2,3-dihydroxypropyl)-2,4,6-triiodoisophthalamide (5.0 g 6.35 mmol). pH is adjusted to pH 2 and a solution of potassium iodide (1.05 g, 6.35 mmol) and iodine 1.61 g, 6.35 mmol) in water (5 ml) and methanol (5 ml) is added drop wise at 50° C. The mixture is stirred over night. The solution is cooled to 10° C. and N,N'-Bis-(2,3-dihydroxy-propyl)-5-formylamino-2,4,6-triiodo-isophthalamide (Example 1a)(4.65 g 6.35 mmol) is added. Potassium hydroxide (10 M) is added drop wise to maintain a stable pH of 11.6 and the mixture is stirred for 24 hours. The solution is diluted with water (50 ml) and treated with ion exchangers (AMB200C, 20 ml) and (IRA67, 20 ml). The resins are filtered off and rinsed with water. The combined aqueous phases are reduced in vacuo and the crude product is purified by preparative HPLC (column Phenomenex Luna C18 10 μm 250×50.0 mm, solvents: A=water and B=acetonitrile; gradient 0-10% B over 60 min; flow 50.0 ml/min.

Example 22

5-(3-(N-(3,5-bis(2,3-dihydroxypropylcarbamoyl)-2,4,6-triiodophenyl)formamido)-2-hydroxypropylamino)-$N^1$,$N^3$-bis(2,3-dihydroxypropyl)-2,4,6-triiodoisophthalamide

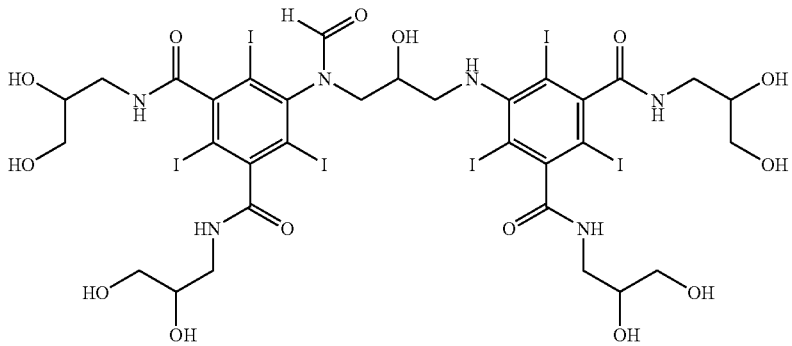 [SMILES: O=CN(CC(O)CNc1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

22a) 5-(N-(3-bromo-2-hydroxypropyl)-2,2,2-trifluoroacetamido)-N¹,N³-bis(2,3-dihydroxypropyl)-2,4,6-triiodo-isophthalamide was prepared according to the literature Ref: Priebe, H.; Dugstad, H.; Heglund, I. F.; Sande, R.; Toenseth, C. P. Synthesis, analysis and toxicity of three compounds formed during the synthesis of iodixanol. Acta Chemica Scandinavica (1995), 49(10), 737-43.

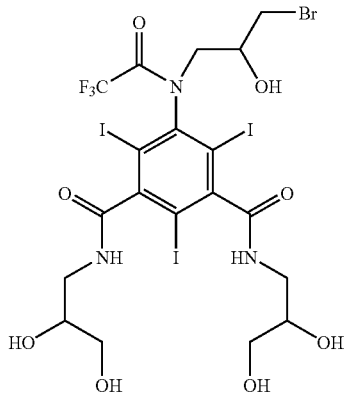 [SMILES: O=C(NCC(O)CO)c1c(I)c(C(=O)NCC(O)CO)c(I)c(N(CC(O)CBr)C(=O)C(F)(F)F)c1I]

22b) 5-(3-(N-(3,5-bis(2,3-dihydroxypropylcarbamoyl)-2,4,6-triiodophenyl)formamido)-2-hydroxypropylamino)-N¹,N³-bis(2,3-dihydroxypropyl)-2,4,6-triiodoisophthalamide N,N'-Bis-(2,3-dihydroxy-propyl)-5-formylamino-2,4,6-triiodo-isophthalamide (Example 1a)(1.1 g, 1.5 mmol) was slurried in water (2 ml) and methanol (0.7 ml). Potassium hydroxide (10 M, 120 ul) was added to give a clear solution with pH 11.3. 5-(N-(3-bromo-2-hydroxypropyl)-2,2,2-trifluoroacetamido)-N¹,N³-bis(2,3-dihydroxypropyl)-2,4,6-triiodoisophthalamide (1.41 g, 1.5 mmol) was dissolved in water (3.0 ml) and added to the reaction mixture at ambient temperature. pH was maintained at 11.5 with additions of potassium hydroxide (10 M). The mixture was stirred for two days and then diluted with water (50 ml) and treated with ion exchangers (AMB200C, 20 ml) and (IRA67, 20 ml). The resins was filtered off and rinsed with water. The combined aqueous phases were reduced in vacuo and the crude product was purified by preparative HPLC (column Phenomenex Luna C18 10 μm 250×75.0 mm, solvents: A=water and B=acetonitrile; gradient 5% isocratic for 5 min, 5-15% B over 35 min; flow 175.0 ml/min, UV detection at 254 nm). After freeze-drying 1.07 g of 5-(3-(N-(3,5-bis(2,3-dihydroxypropylcarbamoyl)-2,4,6-triiodophenyl)formamido)-2-hydroxypropylamino)-N¹,N³-bis(2,3-dihydroxypropyl)-2,4,6-triiodoisophthalamide was obtained (48% yield)

LC-MS-TOF (column Agilent Zorbax SB-Aq C18 3.5 μm 3.0×100 mm, solvents: A=water/0.1% formic acid and B=acetonitrile/0.1% formic acid; gradient 4-15% B over 10 min; flow 0.5 ml/ min, UV detection at 210-240 nm) MS-TOF gave two peaks at 6.14 and 6.67 minutes with [M+H]⁺: 1494.6949, [M+Na]⁺:1516.6769, [M+K]⁺:1532.6509 corresponding to the wanted structure.

What is claimed is:

1. Compounds of formula (I)

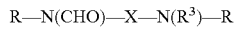    (I)

Formula (I)
and salts or optical active isomers thereof,
wherein
X denotes a $C_3$ to $C_8$ straight or branched alkylene moiety optionally with one or two $CH_2$ moieties replaced by oxygen atoms, sulphur atoms or $NR^1$ groups and wherein the alkylene moiety optionally is substituted by up to six —$OR^1$ groups;
$R^1$ denotes a hydrogen or a $C_1$ to $C_4$ straight or branched alkyl group;
$R^3$ denotes a formyl moiety; and
each R independently is the same or different and denote a triiodinated phenyl group further substituted by two groups $R^2$ wherein each $R^2$ is the same or different and denotes a hydrogen atom or a non-ionic hydrophilic moiety, provided that at least one $R^2$ group in the compound of formula (I) is a hydrophilic moiety.

2. The compound as claimed in claim 1 wherein X denotes a straight $C_3$ to $C_8$ alkylene chain substituted by one to six —$OR^1$ groups.

3. The compound as claimed in claim 1 wherein $R^1$ denotes a hydrogen atom or a methyl group.

4. The compound as claimed in claim 1 wherein X denotes a straight $C_3$ to $C_5$ alkylene chain having at least one hydroxyl group substituted in a position that is not vicinal to the bridge nitrogen atom.

5. The compound as claimed in claim 4 wherein the $C_3$ to $C_5$ alkylene chain is a straight propylene, butylene or pentylene chain substituted by one, two or three hydroxyl groups.

6. The compound as claimed in claim 1 wherein each of the triiodinated phenyl group R denotes a 2,4,6-triiodinated phenyl group further substituted by two groups $R^2$ in the remaining 3 and 5 positions in the phenyl moiety.

7. The compound as claimed in claim 1 wherein each $R^2$ are the same or different and denotes a non-ionic hydrophilic moiety comprising esters, amides and amine moieties, optionally further substituted by a straight chain or branched chain $C_{1-10}$ alkyl group, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

8. The compound as claimed in claim 7 wherein each $R^2$ are the same or different and denote a non-ionic hydrophilic moiety comprising esters, amides and amine moieties, further substituted by a straight chain or branched chain $C_{1-5}$ alkyl groups substituted by 1 to 3 hydroxy groups.

9. The compound as claimed in claim 6 wherein each $R^2$ are the same or different and are polyhydroxy $C_{1-5}$ alkyl, hydroxyalkoxyalkyl with 1 to 5 carbon atoms and hydroxypolyalkoxyalkyl with 1 to 5 carbon atoms attached to the iodinated phenyl group via an amide or a carbamoyl linkage.

10. The compound as claimed in claim 6 wherein each $R^2$ is the same or different and is selected from:
—$CONH_2$;
—$CONHCH_3$;
—CONH—$CH_2$—$CH_2$—OH;
—CONH—$CH_2$—$CH_2$—$OCH_3$;
—CONH—$CH_2$—CHOH—$CH_2$—OH;
—CONH—$CH_2$—$CHOCH_3$—$CH_2$—OH;
—CONH—$CH_2$—CHOH—$CH_2$—$OCH_3$;
—CON($CH_3$)$CH_2$—CHOH—$CH_2$OH;
—CONH—CH—($CH_2$—OH)$_2$;
—CON—($CH_2$—$CH_2$—OH)$_2$;
—CON—($CH_2$—CHOH—$CH_2$—OH)$_2$;
—CONH—$OCH_3$;
—CON ($CH_2$—CHOH—$CH_2$—OH) ($CH_2$—$CH_2$—OH);
—CONH—C($CH_2$—OH)$_2$ $CH_3$;
—CONH—C($CH_2$—OH)$_3$;
—CONH—CH ($CH_2$—OH) (CHOH—$CH_2$—OH);
—NH($COCH_3$);
—N($COCH_3$) $C_{1-3}$ alkyl;

—N(COCH$_3$)—mono, bis or tris-hydroxy C$_{1-4}$ alkyl;
—N(COCH$_2$OH)—hydrogen, mono, bis or tris-hydroxy C$_{1-4}$ alkyl;
—N(CO—CHOH—CH$_2$OH)—hydrogen, mono, bis or trihydroxylated C$_{1-4}$ alkyl;
—N(CO—CHOH—CHOH—CH$_2$OH)—hydrogen, mono, bis or trihydroxylated C$_{1-4}$ alkyl;
—N(CO—CH—(CH$_2$OH)$_2$)—hydrogen, mono, bis or trihydroxylated C$_{1-4}$ alkyl; and
—N(COCH$_2$OH)$_2$.

11. The compound as claimed in claim 10 wherein all R$^2$ groups denote the entity —CONH—CH$_2$—CHOH—CH$_2$—OH.

12. The compound as claimed in claim 1 being selected from the following:
- 5,5'-(2-hydroxypropane-1,3-diyl)bis(formylazanediyl)bis(N$^1$,N$^3$-bis(2,3-dihydroxypropyl)-2,4,6-triiodoisophthalamide);
- 5,5'-(2,3-dihydroxybutane-1,4-diyl)bis(formylazanediyl)bis(N$^1$,N$^3$-bis(2,3-dihydroxypropyl)-2,4,6-triiodoisophthalamide);
- 5,5'-(2,4-dihydroxypentane-1,5-diyl)bis(formylazanediyl)bis(N$^1$,N$^3$-bis(2,3-dihydroxypropyl)-2,4,6-triiodoisophthalamide);
- 5,5'-(2,3,4-trihydroxypentane-1,5-diyl)bis(formylazanediyl)bis(N$^1$,N$^3$-bis(2,3-dihydroxypropyl)-2,4,6-triiodoisophthalamide);
- 5,5'-(2,3-dihydroxybutane-1,4-diyl)bis(formylazanediyl)bis(N$^1$,N$^3$-bis(2,3-dihydroxypropyl)-2,4,6-triiodo-N$^1$,N$^3$-dimethylisophthalamide);
- 5,5'-(2,4-dihydroxypentane-1,5-diyl)bis(formylazanediyl)bis(N$^1$,N$^3$-bis(2,3-dihydroxypropyl)-2,4,6-triiodo-N$^1$,N$^3$-dimethylisophthalamide);
- 5,5'-(2-hydroxypropane-1,3-diyl)bis(formylazanediyl)bis(N$^1$,N$^3$-bis(2,3-dihydroxypropyl)-2,4,6-triiodo-N$^1$,N$^3$-dimethylisophthalamide);
- 5,5'-(2-hydroxypropane-1,3-diyl)bis(formylazanediyl)bis(N$^1$,N$^3$-bis(1,3-dihydroxypropan-2-yl)-2,4,6-triiodoisophthalamide);
- 5,5'-(2,3-dihydroxybutane-1,4-diyl)bis(formylazanediyl)bis(N$^1$,N$^3$-bis(1,3-dihydroxypropan-2-yl)-2,4,6-triiodoisophthalamide);
- 5,5'-(2,4-dihydroxypentane-1,5-diyl)bis(formylazanediyl)bis(N$^1$,N$^3$-bis(1,3-dihydroxypropan-2-yl)-2,4,6-triiodoisophthalamide);
- 5,5'-(2,3-dihydroxybutane-1,4-diyl)bis(formylazanediyl)bis(N$^1$-(2,3-dihydroxypropyl)-N$^3$-(2-hydroxyethyl)-2,4,6-triiodoisophthalamide);
- 5,5'-(2-hydroxypropane-1,3-diyl)bis(formylazanediyl)bis(N$^1$-(2,3-dihydroxypropyl)-N$^3$-(2-hydroxyethyl)-2,4,6-triiodoisophthalamide);
- 5,5'-(2,4-dihydroxypentane-1,5-diyl)bis(formylazanediyl)bis(N$^1$-(2,3-dihydroxypropyl)-N$^3$-(2-hydroxyethyl)-2,4,6-triiodoisophthalamide);
- 5,5'-(2-hydroxypropane-1,3-diyl)bis(formylazanediyl)bis(N$^1$-(1,3-dihydroxypropan-2-yl)-N$^3$-(2,3-dihydroxypropyl)-2,4,6-triiodoisophthalamide);
- 5,5'-(2,3-dihydroxybutane-1,4-diyl)bis(formylazanediyl)bis(N$^1$-(1,3-dihydroxypropan-2-yl)-N$^3$-(2,3-dihydroxypropyl)-2,4,6-triiodoisophthalamide);
- 5,5'-(2,4-dihydroxypentane-1,5-diyl)bis(formylazanediyl)bis(N$^1$-(1,3-dihydroxypropan-2-yl)-N$^3$-(2,3-dihydroxypropyl)-2,4,6-triiodoisophthalamide);
- 5,5'-(2-hydroxypropane-1,3-diyl)bis(formylazanediyl)bis(N$^1$-(1,3-dihydroxypropan-2-yl)-N$^3$-(2-hydroxyethyl)-2,4,6-triiodoisophthalamide);
- 5,5'-(2,3-dihydroxybutane-1,4-diyl)bis(formylazanediyl)bis(N$^1$-(1,3-dihydroxypropan-2-yl)-N$^3$-(2-hydroxyethyl)-2,4,6-triiodoisophthalamide);
- 5,5'-(2,4-dihydroxypentane-1,5-diyl)bis(formylazanediyl)bis(N$^1$-(1,3-dihydroxypropan-2-yl)-N$^3$-(2-hydroxyethyl)-2,4,6-triiodoisophthalamide).

13. A diagnostic agent comprising a compound of formula (I) as defined in claim 1.

14. An X-ray diagnostic composition comprising a compound of formula (I) as defined in claim 1 together with a pharmaceutically acceptable carriers or excipients.

15. A method of imaging, specifically X-ray imaging, comprising administration of compounds of formula (I) as defined in claim 1 to the human or animal body, examining the body with a diagnostic device and compiling data from the examination and optionally analysing the data.

16. A compound of 5,5'-(2-hydroxypropane-1,3-diyl)bis(formylazanediyl)bis(N$^1$,N$^3$-bis(2,3-dihydroxypropyl)-2,4,6-triiodoisophthalamide), and salts thereof.

17. A diagnostic agent comprising a compound as defined in claim 16.

18. An X-ray diagnostic composition comprising a compound as defined in claim 16 together with a pharmaceutically acceptable carriers or excipients.

19. A method of imaging, specifically X-ray imaging, comprising administration of a compound as defined in claim 16 to the human or animal body, examining the body with a diagnostic device and compiling data from the examination and optionally analysing the data.

* * * * *